(12) United States Patent
Kvietok et al.

(10) Patent No.: US 7,481,380 B2
(45) Date of Patent: Jan. 27, 2009

(54) METHODS FOR DELIVERING VOLATILE MATERIALS

(75) Inventors: Frank Andrej Kvietok, Aurora, CO (US); Elizabeth Ann Rohrbaugh, Hamilton, OH (US); Michael Sean Farrell, Terrace Park, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 313 days.

(21) Appl. No.: 11/086,080

(22) Filed: Mar. 22, 2005

(65) Prior Publication Data

US 2005/0161522 A1    Jul. 28, 2005

Related U.S. Application Data

(63) Continuation of application No. PCT/US2004/032332, filed on Oct. 1, 2004.

(60) Provisional application No. 60/507,772, filed on Oct. 1, 2003.

(51) Int. Cl.
*B05B 1/28* (2006.01)
*A61L 9/04* (2006.01)

(52) U.S. Cl. ............... 239/301; 239/6; 239/34; 239/43

(58) Field of Classification Search ............ 239/301, 239/34, 47, 49, 51.5, 58, 59, 11, 55, 6, 43
See application file for complete search history.

(56) References Cited

U.S. PATENT DOCUMENTS

| | | |
|---|---|---|
| 1,994,932 A | 3/1935 | Vidal |
| 2,362,093 A | 11/1944 | Keim |
| 2,597,195 A | 5/1952 | Smith |
| 2,802,695 A | 8/1957 | Johnson |
| 2,804,291 A | 8/1957 | Segerstad |
| 2,847,976 A | 8/1958 | Spaulding |
| 3,283,787 A | 11/1966 | Davis |
| 3,550,853 A | 12/1970 | Gray |
| 3,685,734 A | 8/1972 | Paciorek et al. |
| 3,972,473 A | 8/1976 | Harrison |
| 4,084,732 A | 4/1978 | Dearling |
| 4,145,001 A | 3/1979 | Weyenberg et al. |
| 4,158,440 A | 6/1979 | Sullivan et al. |
| 4,286,754 A | 9/1981 | Jones |
| 4,413,779 A | 11/1983 | Santini |
| 4,454,987 A | 6/1984 | Mitchell |
| 4,605,165 A | 8/1986 | Van Loveren et al. |
| 4,726,519 A | 2/1988 | Muoio |
| 4,780,253 A | 10/1988 | Fukuhara et al. |
| 5,050,798 A * | 9/1991 | Sullivan .................. 239/58 |
| 5,069,231 A | 12/1991 | Rutherford |

(Continued)

FOREIGN PATENT DOCUMENTS

EP    0078114    5/1983

(Continued)

*Primary Examiner*—Davis D Hwu
(74) *Attorney, Agent, or Firm*—Brent M. Peebles; Amy I. Ahn-Roll

(57) ABSTRACT

A method for emitting or releasing volatile materials to the atmosphere is provided. More specifically, a method for delivering one or more volatile materials using a non-aerosol, non-energized volatile material delivery system via an evaporative surface device, without a source of heat, gas, or electrical current, are also provided.

1 Claim, 14 Drawing Sheets

U.S. PATENT DOCUMENTS

| | | | |
|---|---|---|---|
| 5,139,864 A | | 8/1992 | Lindauer |
| 5,242,111 A | | 9/1993 | Nakoenczny et al. |
| 5,361,522 A | * | 11/1994 | Green .................. 40/725 |
| 5,364,027 A | | 11/1994 | Kuhn |
| 5,556,030 A | * | 9/1996 | Paul .................. 239/56 |
| 5,755,381 A | | 5/1998 | Yazaki |
| 5,845,847 A | * | 12/1998 | Martin et al. .................. 239/58 |
| 6,050,551 A | * | 4/2000 | Anderson .................. 261/30 |
| 6,481,639 B1 | * | 11/2002 | Pozzo .................. 239/47 |
| 6,551,560 B1 | | 4/2003 | Flashinski et al. |
| 6,899,280 B2 | * | 5/2005 | Kotary et al. .................. 239/34 |
| 6,913,733 B2 | | 7/2005 | Hardy et al. |
| 6,994,799 B2 | | 2/2006 | Van Driessche et al. |
| 2006/0076429 A1 | | 4/2006 | Kvietok et al. |
| 2006/0097065 A1 | | 5/2006 | Kvietok et al. |

FOREIGN PATENT DOCUMENTS

EP     1076014     12/2004

* cited by examiner

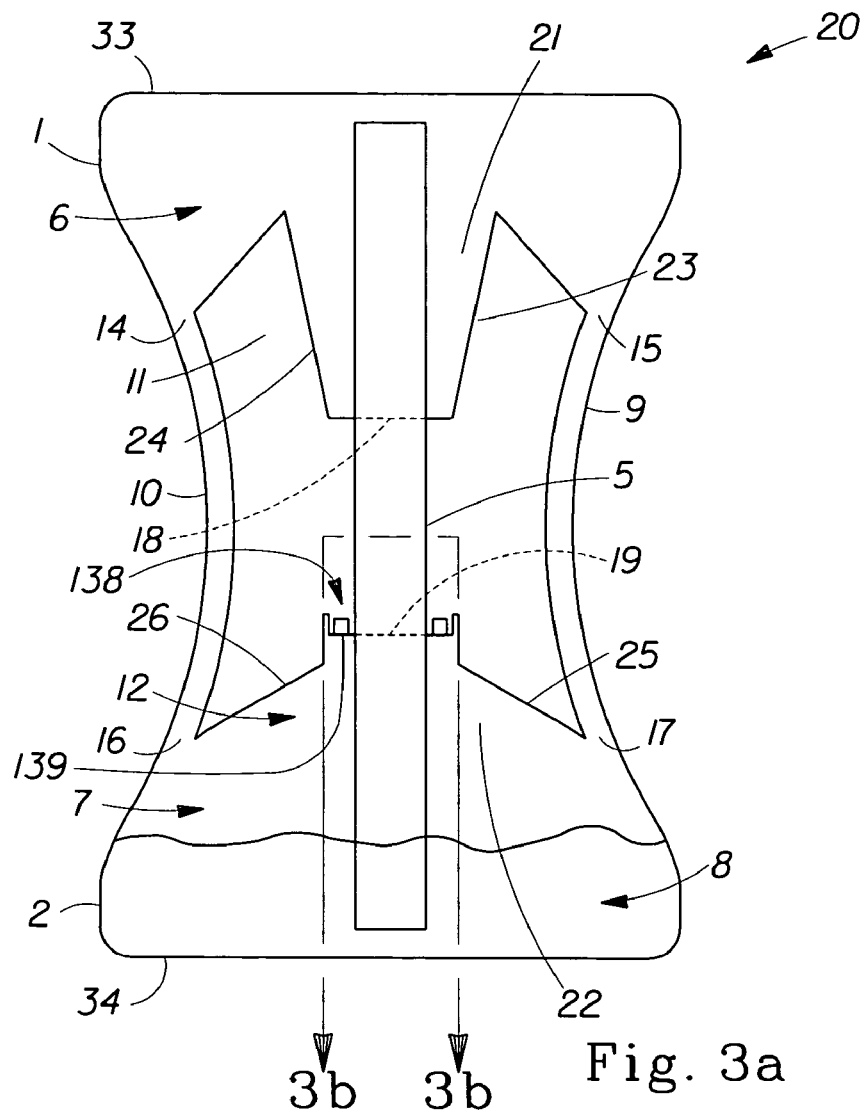
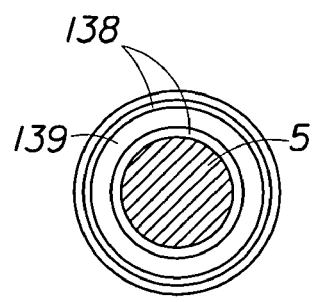
Fig. 3a
Fig. 3b

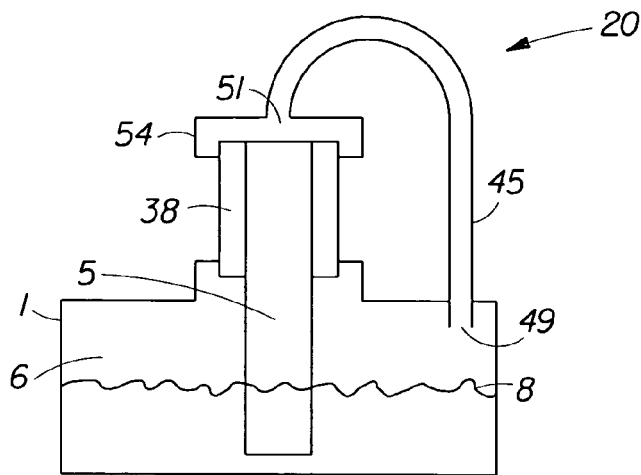
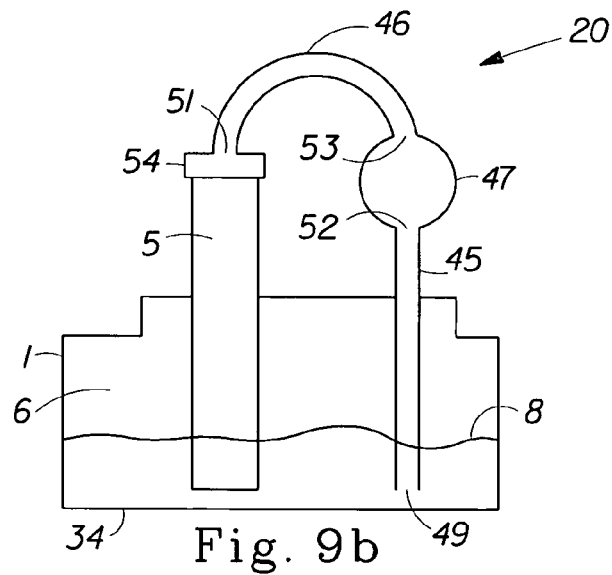
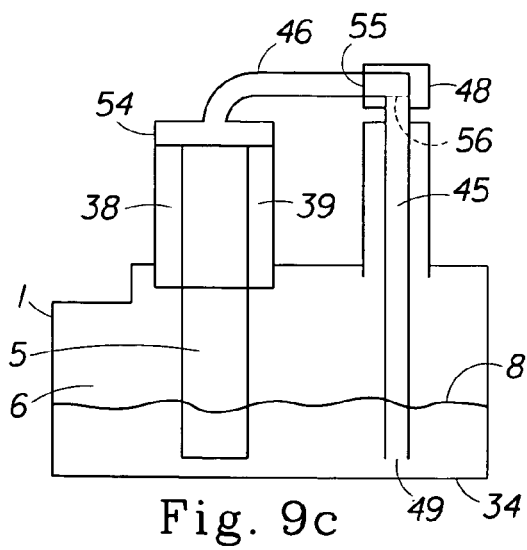

METHODS FOR DELIVERING VOLATILE MATERIALS

CROSS REFERENCE TO RELATED APPLICATION

This application is a continuation application of prior International Application No. PCT/US2004/032332, filed Oct. 1, 2004, designating the U.S. This application also claims the benefit of the filing date of provisional U.S. Patent Application No. 60/507,772 filed Oct. 1, 2003.

FIELD OF THE INVENTION

The present invention relates to methods for emitting or releasing volatile materials to the atmosphere. More specifically, the invention relates to methods for delivering one or more volatile materials from at least one source using a non-energized delivery system containing an evaporative surface device.

BACKGROUND OF THE INVENTION

It is generally known to use a device to evaporate a volatile composition into a space, particularly a domestic space, e.g., a bathroom, to provide a pleasant aroma. The most common of such devices is the aerosol container, which propels minute droplets of an air freshener composition into the air. Another common type of dispensing device is a dish containing or supporting a body of gelatinous matter which when it dries and shrinks releases a vaporized air-treating composition into the atmosphere. Other products such as deodorant blocks are also used for dispensing air-treating vapors into the atmosphere by evaporation. Another group of vapor-dispensing devices utilizes a carrier material such as paperboard impregnated or coated with a vaporizable composition. There are a variety of such devices on sale, for example the ADJUSTABLE® (manufactured by Dial Corp.) or the DUET® 2 in 1 Gel+Spray (manufactured by S.C. Johnson). Generally, these devices consist of a perfume or fragrance source, an adjustable top for fragrance control and/or a sprayer. By the adjustment of the openings in the fragrance source (passive dispenser), there will be a continuous supply of the perfume or fragrance to the space in which the device is placed. By application of the sprayer (active dispenser), there will be a temporary supply of the perfume or fragrance to the space in which the device is delivered.

A problem with such an arrangement is that a person occupying the space will quickly become accustomed to the perfume or fragrance and, after a while, will not perceive the fragrance strength as being as intense or may not notice it at all. This is a well-known phenomenon called habituation. One effort to deal with the problem of habituation is described in U.S. Patent Application Publication No. U.S. Pat. No. 5,755,381, to Seiichi Yazaki. The Yazaki. patent discloses an aroma emission device for emitting aroma from an aromatic liquid for a certain period of time at a uniform level of aroma. The device comprises a vessel that is partitioned via a portioning plate into an upper compartment and a lower compartment, having an air tube penetrating through a top cover portion and a bottom cover portion. Perforation is provided in the portioning plate to allow the upper and lower compartments to communicate with each other. As air is let into the upper compartment, the aromatic liquid held in the upper compartment flows down through the perforation into the partitioning plate and builds up in the empty portion of the bottom compartment. Aroma-laden air is released via the air tube of the lower compartment. When the aromatic liquid in the upper compartment fully transfers into the lower compartment, the emission of the aroma-laden air stops. The device can be repeatedly used by placing the vessel of the device upside down at any time. The Yazaki. patent, however, appears to be directed to a device which can be operated as a water clock. That is, as the fluid travels from upper one compartment to the lower compartment, the device emits an aromatic fragrance and then stops itself when the fluid transfer is complete. The Yazaki patent does not mention the use of evaporative surface devices to deliver the perfume or aromatic fragrance, rather aroma-laden air of the Yazaki device is released via the use of an air tube located in the lower compartment. In addition, the Yazaki aromatic fragrance is delivered as a temporary emission. It is specifically designed not to be continuous.

Evaporative surface device devices (such as, wicking devices) are well known for dispensing volatile liquids into the atmosphere, such as fragrance, deodorant, disinfectant or insecticide active agent. A typical evaporative surface device utilizes a combination of a wick and emanating region to dispense a volatile liquid from a liquid fluid reservoir. Evaporative surface devices are described in U.S. Pat. Nos. 1,994,932; 2,597,195; 2,802,695; 2,804,291; 2,847,976; 3,283,787; 3,550,853; 4,286,754; 4,413,779; and 4,454,987.

Ideally, the evaporative surface device should be as simple as possible, require little or no maintenance and should perform in a manner that allows the volatile material to be dispensed at a steady and controlled rate into the designated area while maintaining its emission integrity over the life span of the device. Unfortunately, nearly all of the relatively simple non-aerosol devices that are commercially available suffer from the same limitation. The emission becomes distorted over the life span of the device due to the fact that the more volatile components are removed first, leaving the less volatile components behind. This change of the composition with time eventually results in a weakening of the intensity of the fragrance since the less volatile components evaporate more slowly. It is these two problems, i.e., the weakening of intensity and distortion over the lifetime of the fragrance material, that have occupied much of the attention of those who seek to devise better air freshener devices. Practically all devices, which depend on evaporation from a surface, suffer from the shortcomings mentioned above. In most of these devices, a wick, gel or porous surface simply provides a greater surface area from which the fragrance material can evaporate more quickly, but fractionation still occurs, as it would from the surface of the liquid itself, resulting in an initial burst of fragrance followed by a period of lower intensity once the more volatile components have evaporated. Due to this fractionation, and perhaps in combination with the clogging of the wick due to precipitation of insolubles, the evaporative surface device begins to malfunction. As the fragrance becomes distorted, the intensity of the emission weakens perceptibly.

Other problems associated with volatile material delivery systems include the steady decline in scent intensity over time, and the limited ability of the consumer to control scent intensity on demand. Attempts to solve these problems often involve combining the features of active and passive dispensers. The goal of these combined devices is to provide the ability to both enhance the atmosphere with a burst of dispersible material for immediate effect, and to provide for a longer lasting, continuous, evaporative effect. An example of such an attempt is set forth in U.S. Pat. No. 3,972,473 of Harrison which teaches a combined spray and evaporative air freshener comprising an aerosol container and an open cup dispenser. Another such dispenser, adapted for combined continuous and instant operation, is described in U.S. Pat. No. 5,364,027 of Kuhn, wherein a deformable container for a liquid dispersible substance is fitted with two immersion tube channels, one terminating in a spray nozzle, the other containing a evaporative surface device or similar absorbent material providing for evaporation of the liquid. Also Muoio, in U.S. Pat. No. 4,726,519, teaches a device for both instant and continuous dispensing of an air treatment composition. The device includes a pressurized container containing an air-treating liquid and an absorbent member. The device can simultaneously spray the air-treating liquid into the air and discharge it into the absorbent member. The device of Dearling, U.S. Pat. No. 4,084,732 may be manipulated and adjusted for simultaneous spraying into the air and recharging of a continuous dispensing means. Another effort is described in EP Patent Publication No. 1076014 to Furner, et al. The Furner patent discloses a dual functional dispenser, which combines active aerosol spray dispensers in combination with passive dispensers of volatile materials. The active dispensers described in the Furner patent encompass the following sprayers: pressurized, aerosol, bellows, air displacement, and pump action dispensers, including fluid reservoirs of compressed gaseous active material.

Like the Yazaki patent, the various devices described by the above publications have a number of practical problems and disadvantages, which make them ineffective and/or uneconomical for use. Consumers want non-energized devices that provide an interactive scent experience which enable them to better enjoy the fragrance through improved consistency over time coupled with periodic bursts of freshness. Though some of the above patents require human interaction, none of the patents describe a non-energized device that can provide a temporary, higher scent intensity on-demand (boost level emission) with an automatic return to the continuous, base line scent intensity (maintenance level emission) without further consumer interaction. For those publications that require evaporative surface device devices, none teach an improvement in scent intensity and character fidelity over time by the periodic reversals in volatile material flow direction on the evaporative surface device. There is no non-energized, non-aerosol spray device disclosed that automatically returns to a base line emission level of volatile materials after providing an intensifying temporary emission level of volatile materials. Furthermore, there is no teaching of a non-energized, non-aerosol device that provides for flushing of the evaporative surface device to reduce the problems associated with volatile material fractionation (such as, partitioning) or clogging of the evaporative surface device.

Solutions to the problems of habituation, scent decline, fractionation, and wick clogging coupled with the ability of a non-energized volatile material delivery system to transform the notion of intensity control into a desirable, rewarding process for consumers have been sought. The improved aesthetics associated with the simplicity of how the boost level emission is provided, and the dynamic interactive scent experience thereby created, coupled with an automatic return to the maintenance level emission, makes the non-energized, non-aerosol device highly desirable.

SUMMARY OF THE INVENTION

There are numerous embodiments of methods for emitting or releasing volatile materials to the atmosphere using the non-energized, non-aerosol volatile delivery systems described herein, all of which are intended to be non-limiting examples. In one aspect of the invention, a method for releasing at least one volatile material to the atmosphere is provided. The steps of the method comprise (a) providing a non-energized volatile material delivery system (hereinafter "delivery system"), and (b) delivering a continuous maintenance level emission of at least one volatile material, and/or a temporary boost level emission of at least one volatile material, wherein the delivery system is free of a source of heat, gas, or electrical current, and wherein the at least one volatile material is not mechanically delivered by an aerosol. The delivery system may further comprise: (a) at least one container comprising at least one fluid reservoir; (b) at least one evaporative surface device opening located in the at least one container; (c) at least one evaporative surface device, having at least some longitudinal exposure, is at least partially located in the evaporative surface device opening and in the fluid reservoir; wherein the evaporative surface device is fluidly connected to the volatile material; (d) optionally at least one by-pass tube; and (e) optionally one or more secondary evaporative surface devices.

The methods described herein made performed for purposes of providing fragrances, air fresheners, deodorizers, odor eliminators, malodor counteractants, insecticides, insect repellants, medicinal substances, disinfectants, sanitizers, mood enhancers, and aroma therapy aids, or for any other purpose using a material that acts to condition, modify, or otherwise charge the atmosphere or the environment. The at least one volatile material may be from a single source, or alternatively from multiple sources. The at least one volatile material may be a composition containing a variety of volatile materials, as well as, non-volatile materials, in any phase or in any amount. The one or more volatile materials may have various volatility rates over the useful life of the delivery system.

In still another aspect of the invention, a method of releasing at least one volatile material to the atmosphere using a kit is provided. The method comprises the steps of (a) providing a kit and (b) delivering a continuous maintenance level emission of at least one volatile material and/or a temporary boost level emission of at least one volatile material to the atmosphere. The kit comprises (a) a package; (b) instructions for use; and (c) a non-energized volatile material delivery system comprising at least one volatile material, wherein said delivery system provides a continuous maintenance level emission of at least one volatile material and/or a temporary boost level emission of at least one volatile material, wherein said delivery system is free of a source of heat, gas, or electrical current, and wherein said volatile material is not mechanically delivered by an aerosol.

BRIEF DESCRIPTION OF THE DRAWINGS

While the specification concludes with claims particularly pointing out and distinctly claiming the invention, it is believed that the present invention will be better understood from the following description taken in conjunction with the accompanying drawings in which:

FIGS. 1, 2, 3a, and 4, 5c, 6, 7a, 7b, 8a, 8b, 8c, 9a, 9b, 9c, 9d, 10a, 10b, 11, 12, 13c, 15a, and 15b show cross-sections of a delivery system.

FIG. 3b shows a cross-section of a delivery system with a gutter.

FIG. 3c shows a top-view of a gutter assembly.

DETAILED DESCRIPTION OF THE INVENTION

Figure 1:
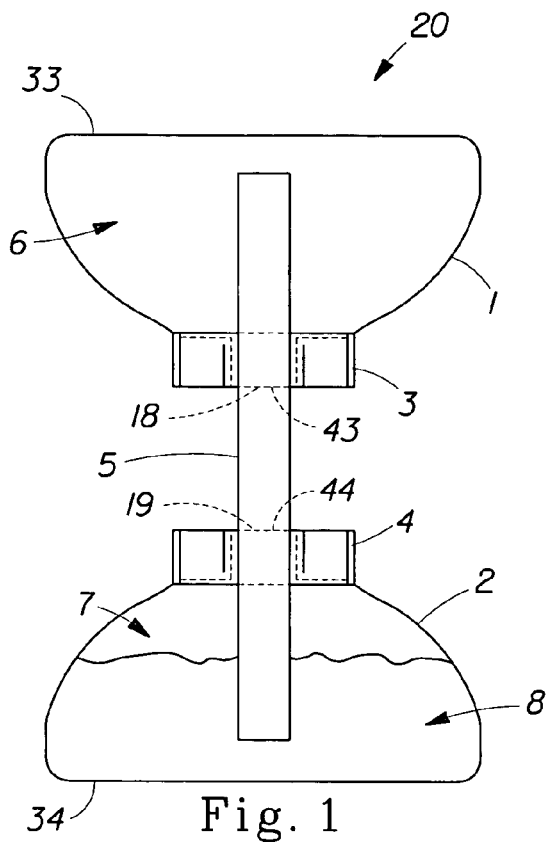

The present invention relates to methods for emitting or releasing volatile materials to the atmosphere. In some embodiments, the invention relates to methods of delivering volatile materials during the maintenance level emission and/or boost level emission modes. In viewing these figures, it should be understood that there are numerous embodiments of the delivery systems described herein, all of which are intended to be non-limiting examples.

Definitions

The term "volatile materials" as used herein, refers to a material or a discrete unit comprised of one or more materials that is vaporizable, or comprises a material that is vaporizable without the need of an energy source. Any suitable volatile material in any amount or form may be used. The term "volatile materials", thus, includes (but is not limited to) compositions that are comprised entirely of a single volatile material. It should be understood that the term "volatile material" also refers to compositions that have more than one volatile component, and it is not necessary for all of the component materials of the volatile material to be volatile. The volatile materials described herein may, thus, also have non-volatile components. It should also be understood that when the volatile materials are described herein as being "emitted" or "released," this refers to the volatilization of the volatile components thereof, and does not require that the non-volatile components thereof be emitted. The volatile materials of interest herein can be in any suitable form including, but not limited to: solids, liquids, gels, and combinations thereof. The volatile materials may be encapsulated, used in evaporative surface devices (e.g. evaporative surface devices), and combined with carrier materials, such as porous materials impregnated with or containing the volatile material, and combinations thereof. Any suitable carrier material in any suitable amount or form may be used. For example, the delivery system may contain a volatile material comprising a single-phase composition, multi-phase composition and combinations thereof, from one or more sources in one or more carrier materials (e.g. water, solvent, etc.).

The terms "volatile materials", "aroma", and "emissions", as used herein, include, but are not limited to pleasant or savory smells, and, thus, also encompass materials that function as fragrances, air fresheners, deodorizers, odor eliminators, malodor counteractants, insecticides, insect repellants, medicinal substances, disinfectants, sanitizers, mood enhancers, and aroma therapy aids, or any other suitable purpose using a material that acts to condition, modify, or otherwise charge the atmosphere or the environment. It should be understood that certain volatile materials including, but not limited to perfumes, aromatic materials, and emissioned materials, will often be comprised of one or more volatile compositions (which may form a unique and/or discrete unit comprised of a collection of volatile materials). For example, a malodor control composition may include, but is not limited to: odor-neutralizing materials, odor blocking materials, odor masking materials, and combinations thereof.

The delivery system may contain volatile materials in the form of perfume oils. Most conventional fragrance materials are volatile essential oils. The volatile materials may comprise one or more volatile organic compounds which are commonly available from perfumery suppliers. Furthermore, the volatile materials can be synthetically or naturally formed materials. Examples include, but are not limited to: oil of bergamot, bitter orange, lemon, mandarin, caraway, cedar leaf, clove leaf, cedar wood, geranium, lavender, orange, origanum, petitgrain, white cedar, patchouli, lavandin, neroili, rose absolute, and the like. In the case of emissioned materials or fragrances, the different volatile materials can be similar, related, complementary, or contrasting.

The volatile material may also originate in the form of a crystalline solid, which has the ability to sublime into the vapor phase at ambient temperatures or be used to fragrance a liquid or a gel. Any suitable crystalline solid in any suitable amount or form may be used. For example, suitable crystalline solids, include but are not limited to: vanillin, ethyl vanillin, coumarin, tonalid, calone, heliotropene, musk xylol, cedrol, musk ketone benzohenone, raspberry ketone, methyl naphthyl ketone beta, phenyl ethyl salicylate, veltol, maltol, maple lactone, proeugenol acetate, evernyl, and the like.

It may not be desirable, however, for the volatile materials to be too similar if the different volatile materials are being used in an attempt to avoid the problem of emission habituation, otherwise, the people experiencing the emissions may not notice that a different emission is being emitted. The different emissions can be related to each other by a common theme, or in some other manner. An example of emissions that are different, but complementary might be a cinnamon emission and an apple emission. For example, the different emissions can provided using a plurality of delivery systems each providing a different volatile material (such as, musk, floral, fruit emissions, etc).

In certain non-limiting embodiments, the maintenance level emission of volatile materials may exhibit a uniform intensity until substantially all the volatile materials are exhausted from the delivery system source at the same time. In other words, when characterizing the maintenance level emission, uniformity can be expressed in terms of substantially constant volatility rates over the life of the volatile material delivery system. The term "continuous," with regard to the maintenance level emission, means that although it is desirable for a delivery system to provide a uniform maintenance level emission mode which continuously emits until all of the volatile materials are substantially depleted (and optionally, for this to occur at approximately the same time in the case where there are one or more sources of the volatile materials), the maintenance level emission can also include periods where there are gaps in emission. The delivery of the maintenance level emission can be of any suitable length, including but not limited up to: 30 days, 60 days, 90 days, shorter or longer periods, or any period between 30 to 90 days.

In certain other non-limiting embodiments, when the boost level emission mode is activated by human interaction, a higher, optionally uniform, intensity of volatile material(s) is emitted over a suitable emission duration, at which time the delivery system can automatically return to delivering volatile material(s) in the maintenance level emission mode without further human interaction. The term "temporary," with regard to the boost level emission, means that though it is desirable for the boost level emissions to emit at a higher intensity for a limited period of time after being activated and/or controlled by human interaction, the boost level emission can also include periods where there are gaps in emissions. Not to be bound by theory, it is believed that the higher intensity of the boost level emission depends upon a number of factors. Some of these factors include, but are not limited to: the "perfume effect" of the volatile material; the volume of the volatile material delivered to the evaporative surface device for purposes of providing a boost level emission; the rate of delivery of the volatile material available from the source for boost level emissions; and the available surface area of the evaporative surface device during the delivery of the boost level emission.

Any suitable volatile material, as well as, any suitable volatile material volume, rate of delivery, and/or evaporative surface area may also be used to raise and/or control the intensity of the boost level emission. Suitable volumes, rates of delivery, and surface areas are those in which the boost level emission exhibits an emission intensity greater than or equal to the maintenance level emission. For example, by providing a greater volume of volatile material to the evaporative surface device, the intensity of the boost level emission may be an increased and/or controlled by the consumer. The volume of the volatile material delivered to the evaporative surface device may also be controlled using a specific dosing device having a specific volume. A collection basin may be used to force a certain volume through the evaporative surface device. The collection basin may be made of any suitable material, size, shape or configuration and may collect any suitable volume of volatile material. For example, the delivery system may comprise a collection basin, such as a unit dose chamber, that may be at least partially filled with at least some of the volatile material to activate the boost level emission. The unit dose chamber provides a controlled volume of the volatile material to an evaporative surface device, such as a evaporative surface device. Other dosing devices may include pumps and spring-action devices.

The term "evaporative surface device" includes any suitable surface that allows for at least some evaporation of volatile materials. Any suitable evaporative surface device having any suitable size, shape, form, or configuration may be used. Suitable evaporative surface devices made from any suitable material, including but not limited to: natural materials, man-made materials, fibrous materials, non-fibrous materials, porous materials, non-porous materials, and combinations thereof. The evaporative surface devices used herein are flameless in character and include any device used for dispensing any type of volatile material (e.g. liquids) into the atmosphere (such as fragrance, deodorant, disinfectant or insecticide active agent). In certain non-limiting embodiments, a typical evaporative surface device utilizes a combination of a wick, gel, and/or porous surface, and an emanating region to dispense a volatile liquid from a liquid fluid reservoir.

As stated above, any suitable increase in the rate of delivery or evaporative surface area is useful in raising and/or controlling the intensity of the boost level emission. The "rate of delivery" relates to the time the volatile material has to evaporate on the evaporative surface device before being returned to a container or fluid reservoir for storage. Suitable means for delivering the volatile material to the evaporative surface device may include, but is not limited to: inversion, pumping, or by use of a spring-action device. For example, the addition of one or more evaporative surface devices (such as, primary wicks or secondary wicks) to the delivery system may be used to increase the surface area in order to increase intensity. The surface area of the secondary evaporative surface device can range from about 1 to about 100 times greater than the surface area of the primary evaporative surface device. Optionally, the secondary evaporative surface device may be in fluid communication with other evaporative surface devices.

In certain non-limiting embodiments, the boost level emission may comprise volatile material emissions from both a primary evaporative surface device and/or a secondary evaporative surface device. The boost level emission may exhibit a boost emission profile of any suitable emission duration. For example, suitable boost level emission durations may include, but are not limited to, durations from less than or equal to 10 minutes; or from about 10 minutes to about 2 hours; and alternatively, from about 2 hours to about 24 hours.

In some non-limiting embodiments, the delivery system may maintain its character fidelity over time with periodic reversals in volatile material flow direction on the evaporative surface device. For example, over time the character fidelity of the delivery system may decrease due to fractionation (such as, partitioning effects) of at least one volatile material or by wick clogging. The solution to both fractionation and wick clogging is to provide a suitable flow reversal on the evaporative surface device over a suitable duration. For example, a suitable flow reversal of the evaporative surface device may consist of the activation of the boost level emission and emission over a suitable duration. In this case, volatile material flow reversal of the evaporative surface device resulting from inversion, pumping or by spring-action can substantially flush the wick in a manner sufficient to clear away some of the unwanted insoluble precipitates, fractionation and/or partitioning effects. Thus, character fidelity is at least partially restored by flushing the wick during the boost level emission. In this way, the consumer can revive the dynamic interactive scent experience by sensing the entire range of different volatile materials contained in the delivery system is a simple step.

In other non-limiting embodiments, the delivery system described herein may be used for such things as fragrancing, malodor control, and insect repellant. For example when placed in a room, or optionally outdoors, such as on a picnic table, insect control, besides fragrancing and malodor control, can be achieved by adjusting the emission levels depending upon the number of insects in the immediate area. When the insect annoyance is small, the maintenance level emission will likely be adequate to provide consumer comfort. However, when bothered by numerous insects, such as mosquitoes and biting flies, the consumer may choose to deliver the boost level emission.

Figures

FIG. 1 depicts a cross-section of a non-limiting embodiment of a delivery system 20 comprising at least one container 1 (and 2) comprising at least one wick opening 18 (and 19), at least one wick 5, at least one fluid reservoir 6 (and 7), and at least one volatile material 8. The delivery system and its components may be made in any suitable size, shape, configuration, or type, and from any suitable material. Suitable materials include, but are not limited to: metal, glass, natural fiber, ceramic, wood, plastic, and combinations thereof. The container 1 (and 2) may comprise the exterior surface of the delivery system 20, as such is subject to visual inspection as well as being picked up and manipulated by the consumer during use, or it may be housed in a shell (not shown). The wick 5 has at least some portion exposed to the atmosphere. The wick opening 18 (and 19) may be of any convenient size and shape and may located anywhere on the container 1 (and 2). The at least one wick opening 18 (and 19) allows a means of delivering the volatile material 8 to the atmosphere via the at least one wick 5 during the maintenance level emission and/or boost level emission modes. In certain non-limiting embodiments, the container 1 (and 2) may be housed in a outer shell (not shown) which is desirably visually attractive and of suitable dimensions that it may be left in view in the area of usage for greatest effectiveness during evaporative dispensing. When more than one container 1 and 2 is present, they may be opposedly-connected and/or fluidly-connected as shown.

In one non-limiting embodiment, the containers 1 and 2 are in fluid-communication via an evaporative surface device comprising a wick 5 having at least some longitudinal exposure to the atmosphere. The container 1 (and 2) may be attached to any other suitable component of the delivery system 20. For instance, containers 1 and 2 may be attached to each other via the wick 5, as part of a shell or housing (not shown), or by any other suitable means. The wick 5 is in fluid contact with at least some volatile material 8 some of the time. The volatile material 5 may be stored in either fluid reservoir 6 or 7. The longitudinal portion of the wick 5 provides enough exposed wick 5 surface area to allow suitable emission rates of the volatile material 8 during both the maintenance level emission and boost level emission modes. Once connected, containers 1 and 2 and their corresponding fluid reservoirs 6 and 7 may be in fluid-communication with each other via the wick 5 or by any other suitable means (e.g. an enclosed channel or tube). Besides providing an evaporative surface for emissions, another purpose for connecting containers 1 and 2 with a wick 5 is to provide a way for excess volatile material 8, which is not evaporated or emitted, to be transported from the upper container 1 by gravity for collection and storage within the lower container 2 without substantial leaking when the delivery system 20 is inverted by the consumer.

The wick fitting 3 (and 4) may function as a seal to hold at least some volatile material 8 in the delivery system 20. The wick fitting 3 (and 4) may be made of any suitable material in any suitable size, shape or configuration so as to sealably attach the wick 5 and/or any component to any component within the delivery system 20. The wick fitting 3 (and 4) may be attached to any portion of the delivery system 20 such that it aids in wick 5 loading and dosing without allowing substantial leakage of the volatile material 8 from the non-wick portion of the delivery system 20. The wick fitting 3 (and 4) may be inserted in the wick opening 18 (and 19), which is located in any suitable location on the container 1 (and 2) surface, such that the wick 5 or any other suitable component (not shown) may pass through the wick opening 18 (and 19) and enter at least a portion of the fluid reservoir 6 (and 7). The at least one wick opening 18 (and 19) and wick fitting 3 (and 4) are dimensioned to both accommodate the wick 5 and any other component, and to minimize excess volatile material 8 leakage from the delivery system 20 if the delivery system 20 is inverted or overturned by the consumer.

The wick 5 may made of any suitable material in any suitable size, shape, or configuration, such that it functions as an wick to allow emission of the volatile material 8 by having at least some portion exposed to the atmosphere. The wick 5 may be located in any suitable location within the container 1 (and 2). The wick 5 may be at least partially located in the container 1 (and 2), the wick opening 18 (and 19), and/or the wick fitting 3 (and 4), being fluidly connected to the volatile material 8, which is stored in the fluid reservoir 6 (and 7) of the container 1 (and 2). The wick 5 may extend inside of the fluid reservoir 6 (and 7) to the container base 33 (and 34). Conversely, the wick 5 may be of any suitable length which will maintain the fluid connection with even a small amount of volatile material 8 in the at least one fluid reservoir 6 (and 7) while in the maintenance level emission mode throughout the useful life of the delivery system 20. There is no particular wick 5 length requirement inside or outside the container 1 (and 2). The at least one wick 5 may be positioned at any desired internal depth within the fluid reservoir 6 (and 7). The at least one wick 5 can optionally occupy the full internal length of the both fluid reservoirs 6 and 7 to maximize the emission delivery of the volatile material 8.

The wick 5 is sealably fastened to the container 1 (and 2) in the location of the at least one wick opening 18 (and 19) via the wick fitting 3 (and 4). The wick fitting 3 (and 4) may sealably hold at least a portion of the wick 5 and other suitable component passing through the wick opening 18 (and 19). The wick fitting 3 (and 4) may fit snuggly around the at least one wick opening 18 (and 19) and the at least one wick 5, respectively, so as to prevent unwanted leakage of the volatile material 8 from the delivery system 20 in storage, during wick 5 loading or dosing of the wick 5 after inversion, pumping or by spring-action, or if toppled. The wick fitting 3 (and 4) may be affixed by any means (such as by friction, adhesion, etc) to the container 1 (and 2) so as to minimize unwanted volatilization of the volatile material 8 especially when not in use. The wick fitting 3 (and 4) may be optionally vented (not shown) in any suitable location so as to aid loading of the wick 5.

There may be at least one container base 33 (and 34) to aid in stabilizing and/or hold the delivery system 20 in the proper configuration, such as, in the upright position during the maintenance level emission mode. The delivery system 20 may further comprise an additional resealable seal (not shown) for containing the volatile material in the container 1 (and 2). The delivery system 20 may further have a package seal (not shown) for covering the at least one wick 5 and/or delivery system 20 containing one or more of the volatile materials 8 described above when desired by the manufacturer or consumer, for instance, when the volatile material 8 is not desired to be emitted such as prior to sale or during extended periods away from the room to be fragranced.

Figure 2:
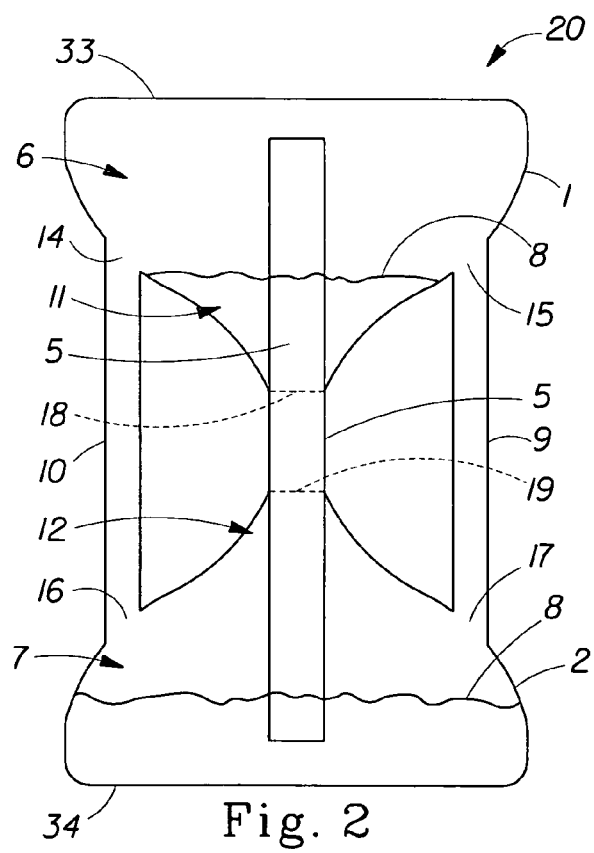

FIG. 2a depicts a cross-section of another non-limiting embodiment of a volatile material delivery system 20 having two containers 1 and 2 which are opposedly-connected and fluidly-connected to each other via at least one by-pass tube 9 (and 10) and/or the at least one wick 5. As above, the containers 1 and 2, having fluid reservoirs 6 and 7 for containing at least some volatile material 8, are fluidly connected via the at least one wick 5 and/or the by-pass tube 9 (and 10). The by-pass tube 9 (and 10) may connect to the container 1 (and 2) via a by-pass tube openings 15 and 17 (14 and 16) having any size, shape, or configuration. The by-pass tube 9 (and 10) may be formed as an integral component of the container 1 (and 2) or may provided as a separate component which is added to the container 1 (and 2). The by-pass tube 9 (and 10) may be made of any suitable material which is compatible with the container 1 (and 2) such that it may be suitably sealed or connected to the container 1 (and 2) and/or fluid reservoir 6 (and 7) in any configuration without fluid leakage. The by-pass tube openings 15 and 17 (14 and 16) allow for direct fluid communication of the volatile material 8 between the fluid reservoirs 6 and 7 via the by-pass tube 9 (and 10). The by-pass tube 9 (and 10), as well as the by-pass tube openings 14 and 16 (15 and 17) may be configured so as to allow for any suitable type of flow desired. The by-pass tube 9 (and 10) and/or the by-pass tube openings 14, 15, 16, and/or 17 may be each structurally modified to provide for open flow, one-way flow, restricted flow, or combination thereof, of any fluid that passes through these structures. For example, by-pass tube openings 14 and 17 may be made with unrestricted flow while by-pass tube openings 15 and 16 may be made to collect fluid from only one direction or have a reduced flow to provide for aesthetic benefits, such as a dripping. This unique flow configuration gives the delivery system 20 the ability to provide the consumer with unusual visual interests since a modified flow of a volatile material 8 may attract attention to the delivery system. It is possible for each container 1 (and 2) to share a portion of one or more fluid reservoirs 6 (and 7) such that at least some volatile material 8 may be present within the delivery system 20 in any particular location at any time. Such a container 1 (and 2) could, for instance, hold a least some volatile material 8 in both fluid reservoir 6 and fluid reservoir 7 immediately after loading or dosing of the wick 5 by inversion, pumping, or by spring-action. The volatile material 8 itself may also comprise any suitable adjunct ingredient in any suitable amount or in any suitable form. For example, dyes, pigments, and speckles may provide additional aesthetic benefits, especially when observed by the consumer during a modified flow configuration.

The by-pass tube 9 (and 10) may also serve both as an additional fluid reservoir for collecting a certain amount of the volatile material 8, and/or a means to divert a portion of a certain volume of volatile material 8 between the opposing fluid reservoirs 6 and 7 after mixing, pumping or inversion. For example, should the delivery system 20 be toppled off its base 34 from the upright vertical position to a horizontal position, the delivery system 20 may be designed to come to rest in a configuration such that at least one by-pass tube 9 or 10 is located so that it may collect at least some volatile material 8 from each fluid reservoir 6 and 7. In this case, the by-pass tube 9 or 10 acts as an additional fluid reservoir to decrease the potential for unwanted spillage and/or the escape of the volatile material 8 from the delivery system 20.

The wick opening 18 (and 19) may be located anywhere on the exterior surface of the container 1 (and 2). For instance, the wick opening 18 (and 19) may be positioned on the exterior surface of the container 1 (and 2) such that it lies on a plane parallel to the plane of the container base 33 (and 34). A unit dose chamber 11 (and 12) may be located anywhere within the container 1 (and 2), and is generally within the fluid reservoir 6 (and 7). The unit does chamber 11 (and 12) is defined by the interior volume created within the fluid reservoir 6 (and 7) between the uppermost region of the at least one wick opening 18 (and 19) and the lowermost region of the by-pass tube openings 14 and 15 (16 and 17). The actual volume of unit dose chamber 11 (and 12) can vary depending on the size of the at least one fluid reservoir 6 and 7, the volume occupied by the at least one wick 5, and the amount of volatile material 8 delivered to the at least one unit dose chamber 11 and 12 upon inversion of the delivery system 20. In certain non-limiting embodiments, the consumer can control the volume of volatile material delivered to the wick 5 via the unit dose chamber 11 (and 12) by adjusting the loading and/or dosing of the unit dose volume. This may be accomplished for example, by adjusting the amount of volatile material 8 pumped, or by manipulating the inversion of the container 1 (and 2), or by any other suitable means.

When inverted the delivery system 20 may route excess volatile material 8 from the upper fluid reservoir 6 of container 1, which is not collected in the at least one unit dose chamber 11 or absorbed by and/or is loaded onto the at least one wick 5, via the by-pass tubes 9 and 10 via by-pass tube openings 14 and 15 to the lower fluid reservoir 7 via by-pass tube openings 16 and 17 for collection and storage in container 2. For example, the unit dose chamber 10 (and 11) may contain at least some of the volatile material 8 upon inversion of the delivery system 20 and/or the container 1 (and 2). When the delivery system 20 and/or the container 1 (and 2) is inverted and/or toppled from its upright position, the by-pass tube 9 (and 10) fill with some of the volatile material 8 released from the one or more fluid reservoir 6 (and 7), from the at least one unit dose chamber 11 9 and 12), and/or from the wick 5.

When the unit dose chamber 11 in the upper fluid reservoir 6 is at least partially filled, loaded and/or dosed with at least some of the volatile material 8, the unit dose chamber 11 will deliver a controlled volume (e.g. unit dose) of the volatile material 8 to the wick 5 to provide the boost level emission to the atmosphere. What excess volatile material 8 that is not evaporated or emitted will be transported by the wick 5 and collected in the lower fluid reservoir 7 without substantial leakage. The delivery system 20 is also capable of delivering multiple controlled volumes and/or unit doses to enable the initiation of multiple boost level emissions for one or more of the following purposes: fragrancing, malodor control, insect repellency, mood setting, and combinations thereof. The dosing process allows a consumer to deliver a temporary boost level emission to a space whenever needed, for example for malodor control.

Dosing of the wick 5 can be performed by any suitable means, for example, by inversion, by squeezing a bladder, by non-aerosol pumping, or by any other suitable means excluding the use of heat, gas, or electrical current. For example, dosing may occur by inversion when the consumer simply turns the delivery system 20 upside down, setting the delivery system 20 on the container base 33 (and 34). Thus upon inversion, the volatile material 8 that was originally stored in the lower fluid reservoir (6 or 7) is temporarily positioned in the upper fluid reservoir (6 or 7). The volatile material 8 begins to immediately drain from the upper fluid reservoir (6 or 7) and pass to the lower fluid reservoir (6 or 7) via gravity through the unit dose chamber (11 or 12), the wick 5, and/or the by-pass tube 9 (and 10). Once the volatile material 8 is collected in the dose chamber 11 (and 12), the boost level emission begins as the volatile material 8 is delivered to the at least one wick 5 via gravity along the portion of the wick 5 exposed to the atmosphere. When a controlled volume of the volatile material 8 is delivered to the one wick 5 via the unit dose chamber 11 (and 12), the boost level emission may be substantially uniform in terms of volatility rates of volatile material 8, over the a portion of the life of the delivery system 20.

In one non-limiting embodiment, at least some of the unit dose of volatile material 8 in the upper fluid reservoir (6 or 7) that passes from the unit dose chamber 11 (and 12) through the wick opening 18 (and 19) and the wick 5 will be emitted to the atmosphere. That portion of the unit dose that is not emitted may be delivered back to the lower fluid reservoir (6 or 7) via the wick 5 and/or the wick opening 19 (and 18). Once the unit dose chamber 11 (and 12) in the upper fluid reservoir (6 or 7) is drained by gravity, the boost level emission beings to slowly subside until unit dose either is emitted or passes through to the lower reservoir (6 or 7). When the boost level emission ceases, the maintenance level emission automatically returns. In the maintenance level emission mode, the wick 5 draws volatile material 8 stored in the lower fluid reservoir (6 or 7) via capillary action to at least some portion of the wick that exposed to the atmosphere. For example, the volatile material 8 may be emitted from the full length, or any portion thereof, of the exposed longitudinal wick 5 surface between wick openings 18 and 19.

FIG. 3a depicts a cross-section of another non-limiting embodiment of a volatile material delivery system 20 having two containers 1 and 2 which are opposedly-connected and fluidly-connected to each other via by-pass tubes 9 and 10 and/or the wick 5. In this embodiment, by-pass tubes 9 and 10 are configured in such a manner as to create a convenient concave hand hold for ease of placement of the delivery system 20 and to provide protection of the wick 5 from damage if the delivery system 20 is inverted and/or toppled from its upright position and not placed on its container base 33 (and 34).

In one non-limiting embodiment, the volume of the unit dose chamber for the boost level emission may be defined by the volume of volatile material 8 in the upper fluid reservoir (6 or 7) not collected by the by-pass tube 9 (and 10) for channeling back down to the lower fluid reservoir (6 or 7). The unit dose chamber walls 23, 24, 25 and 26 may be configured and located anywhere within the reservoir 6 (and 7) and/or the container 1 (and 2). For example, the unit dose chamber 12 may have chamber walls 25 and 26 that are configured below the by-pass tube openings 16 and 17. The unit dose volume is then collected by the open end 22 of the unit dose chamber walls 25 and 26. Conversely, other configurations of the chamber walls are also useful. For example, the volume of the unit dose collected by the unit dose chamber 11 may be independent of the configuration by-pass tube 9 (and 10) and/or the by-pass tube openings 14 and 15. The unit dose chamber 11 may be located within the fluid reservoir 6 having walls 23 and 24 that extend above the location of the by-pass tube openings 14 and 15. Here a unit dose volume of volatile material 8 in the upper reservoir 6 may be collected in the unit dose chamber 11 via the open end 21 of the unit dose chamber walls 23 and 24 upon inversion, pumping or by spring-action of the delivery system 20.

FIG. 3b depicts a cross-section of another non-limiting embodiment of a volatile material delivery system 20 having a gutter assembly. A gutter 138, located near the wick opening 18 (and 19) on the exterior surface of the container 2, is provided to collect excess volatile material 8 that may escape from the wick 5 and/or the wick opening 18 (and 19) after wick 5 loading and/or toppling of the delivery system 20. Any gutter 138 of any size, shape, configuration, or material may be used. In one non-limiting embodiment the gutter is located in the area in or adjacent to the location of the wick opening 19. In order to catch or collect excess volatile material 8 that may drip out of the opposing wick opening 19 and/or off the wick 5 (such as, after excessive loading by inversion, pumping and/or tipping) an absorbent material 139 is provided. Any suitable absorbent material 139 may be used in any suitable size, shape, or configuration. The absorbent material 139 may be made from any suitable materials that can substantially absorb and/or facilitate evaporation of the volatile material 8. The absorbent material 139 may comprise any suitable evaporative surface material. For example, suitable absorbent material 139 may include paper, plastic, sponge, etc. Excess volatile material 8 that is collected in the gutter 138 may then be absorbed or reabsorbed by absorbent material 139 and redirected to the wick 5, the wick opening 19, or allowed to evaporate directly to the atmosphere.

In certain other non-limiting embodiments, an absorbent material 139 may be placed in or near the location of the gutter 138 so as to aid in the collection of excess volatile material 8 that is not collected by the lower fluid reservoir 7. For example, the absorbent material 139 may be made from wick 5 material in the shape of a thin washer or doughnut that is located in the gutter 138 and surrounds the at least one wick 5. FIG. 3c depicts a top view of the gutter assembly comprising the wick 5, the gutter 138 and the absorbent material 139 in the shape of a thin washer or doughnut. It should be noted that the absorbent material 139 does not have to be in physical contact with either the wick 5 or the wick opening 19. It may be attached to any part of the exterior surface of the delivery system 20 by any suitable means (such as by friction, adhesion, fasteners, etc.). In fact, it does not have to be fixedly attached at all since it can be added or removed by the consumer as desired. The absorbent material 139 can freely slide along the longitudinal axis of the at least one wick 5 coming to rest in the area of the opposing gutter (not shown) wherein it can collect any excess volatile material 8 that may be present in the vicinity of the opposing wick opening (not shown), for example, during inversion, excess pumping, or toppling of the delivery system 20.

Figure 4:
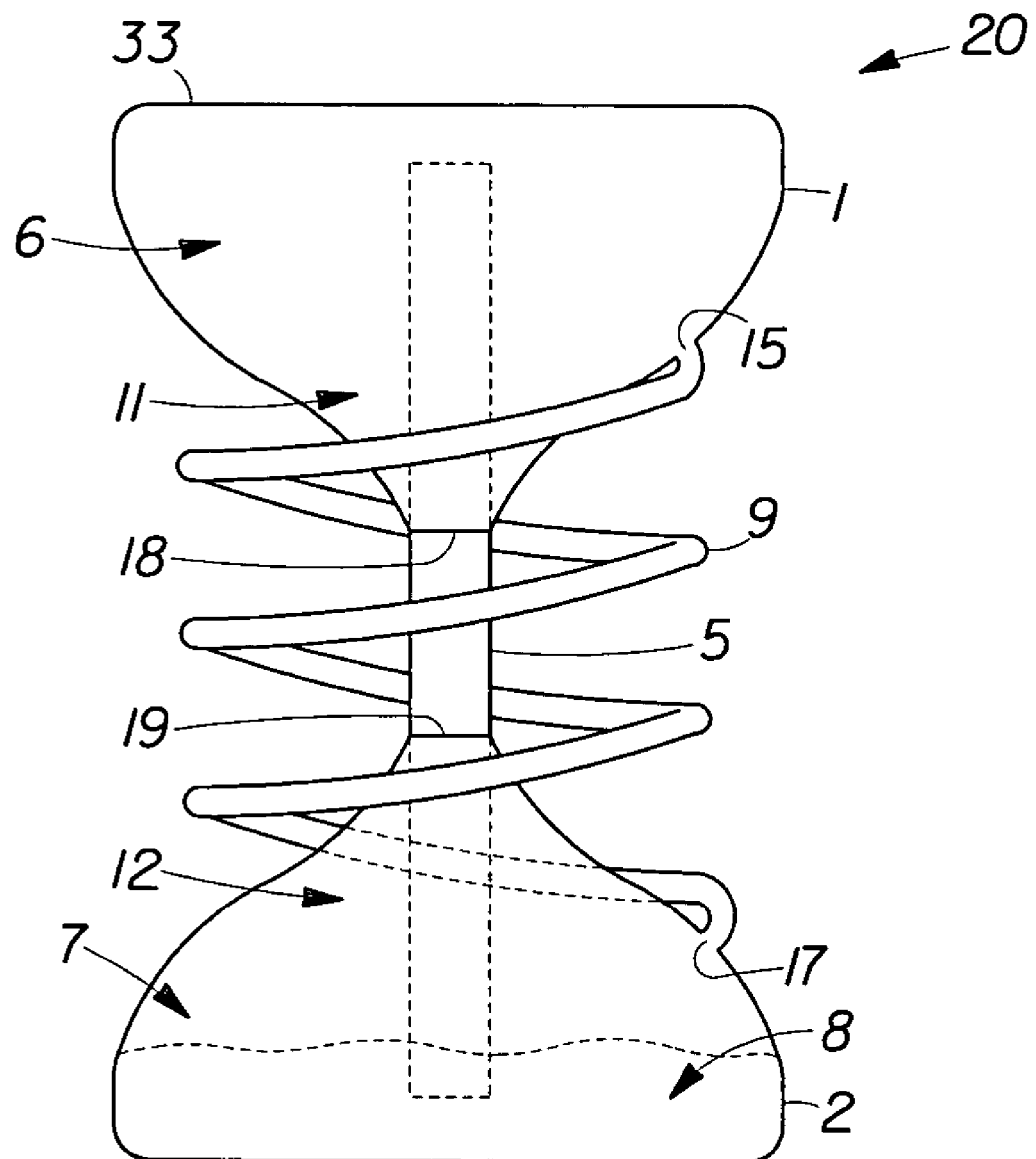

FIG. 4 depicts another non-limiting embodiment of a volatile material delivery system 20 having two containers 1 and 2 which are opposedly-connected and fluidly-connected to each other via a single by-pass tube 9 and/or the at least one wick 5. The by-pass tube 9 may take any suitable size, shape, or configuration and be made of any suitable material. The by-pass tube 9 may be connected to the container 1 (and 2) by any suitable means at any suitable location. For instance, the by-pass tube 9 of similar material as the container 1 (and 2) may be formed in the shape of a spiral, sphere, or ellipse and is connected to the reservoir 6 (and 7). The by-pass tube 9 may be part of any component of the delivery system 20. For example, the by-pass tube 9 may be integrated in the container 1 (and 2) and/or in the wick 5. The by-pass tube 9 may have one or more by-pass tube opening 15 (and 17) which allow fluid communication with the container 1 (and 2) without loss due to leaking or vaporization. For example, the volatile material 8 may flow by gravity after inversion from the upper reservoir 6 to the lower reservoir 7 via the by-pass tube 9 and/or the at least one wick 5. The by-pass tube opening 15 (and 17) may be located anywhere on the surface of the container 1 (and 2) and may be located in such a manner as to allow the formation of a unit dose chamber 11 (and 12), located in the interior space of fluid reservoir 6 (and 7) between the wick opening 18 (and 19) and the by-pass tube opening 15 (and 17), for delivery of the optionally uniform, temporary boost level emission. The by-pass tube 9 may surround the wick 5 so as to protect the wick 5 from physical tampering or damage if the delivery system 20 is inverted and/or toppled from its upright position. This configuration aids in protecting children from unwanted or direct exposure to the volatile material 8 by discouraging contact with the wick 5.

Figure 5A:
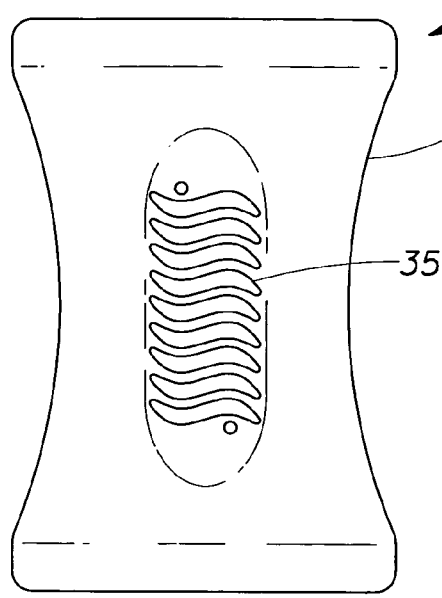
FIG. 5a show side views of a delivery system.
Figure 5B:
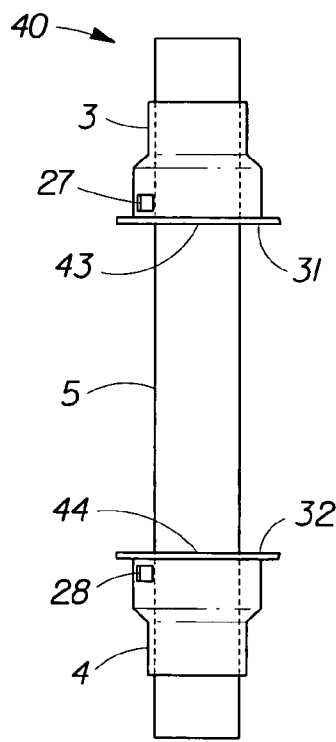
FIG. 5b shows a cross-section of an evaporative surface device.
Figure 5C:
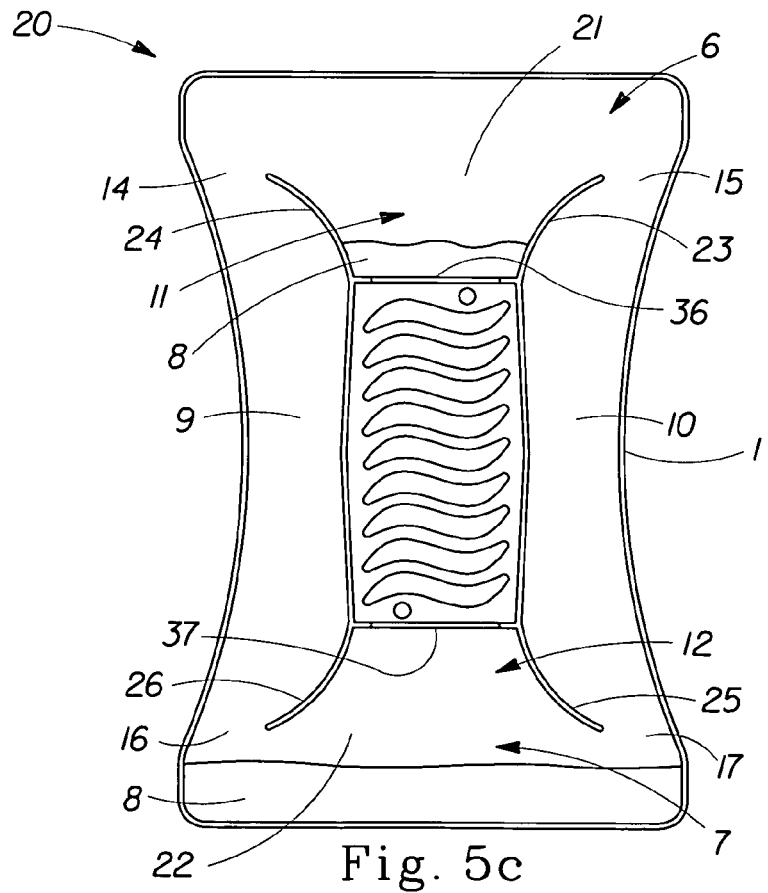

FIGS. 5a, 5b, 5c depict another non-limiting embodiment of a volatile material delivery system 20. FIG. 5a depicts the exterior surface of a single integrated container 1 having one or more vent openings 35 on the integrated container 1. The one or more vent openings 35 allow the volatile material (not shown) to be emitted or delivered from the wick (not shown) to the atmosphere of the room or rooms that require treatment. Optionally, an adjustable vent (not shown) may be added to the container 1 of the delivery system 20 so that the width of the one or more vent openings 35 may be made adjustable and/or closeable. This allows the maintenance and boost level emission rates to be controlled by the consumer. The adjustable vent (not shown) may be made of any suitable material, be of any suitable size or shape, and be located anywhere on or within the delivery system 20. For example, a consumer may open, partially open, partially close, or close the one or more vent openings 35 by moving the adjustable vent (not shown) such that the desired amount of emission is delivered to the location needing treatment.

FIG. 5b depicts a non-limiting embodiment of a evaporative surface device 40 having a wick 5, a wick fitting 3 (and 4), a wick fitting opening 43 (and 44), an optional wick fitting vent hole 27 (and 28), and a wick fitting flange 31 (and 32). All components of the evaporative surface device 40, may be made of any suitable material, and be of any suitable size, shape, or configuration. Each end of the at least one wick 5 may sealably fit into the wick fitting opening 43 (and 44) of the wick fitting 3 (and 4) so as to allow for fluid communication between fluid reservoirs (not shown) via the wick 5 but reduce unwanted leakage of the volatile material (not shown) from around the wick fitting opening 43 (and 44), the wick openings (not shown), or the container (not shown) during use or storage.

FIG. 5c depicts a cross-section of another non-limiting embodiment having a single integrated container 1 having two fluid reservoirs 6 and 7 which are opposedly-connected and fluidly-connected to each other via by-pass tubes 9 and 10 and/or the at least one wick 5. In this embodiment, the by-pass tube 9 (and 10) is configured within the interior of the single integrated container 1 in such a manner as to create a convenient concave hand hold for ease of placement of the delivery system 20 and to provide protection of the wick 5 from damage during inversion and/or if the delivery system 20 toppled from its upright position. The unit dose chamber 11 (and 12) is located within the fluid reservoir 6 (and 7) of the single integrated container 1. The one unit dose chamber 11 (and 12) can have walls 23 and 24 (25 and 26) in the shape of a cup with an open end 21 (and 22) for collection of the volatile material 8 when the delivery system 20 is inverted. The unit dose chamber 11 (and 12) may contain at least some of the volatile material 8 at anytime, especially immediately after inversion. The volatile material 8 may flow by gravity or by non-aerosol pump (not shown) via the by-pass tube 9 (and 10) and/or the wick 5 to the opposing fluid reservoir (6 or 7). The at least one wick opening 18 (and 19) allows penetration of the wick 5 to the fluid reservoir 6 (and 7). The unit dose chamber walls 23 and 24 (25 and 26) may extend above the by-pass tube openings 14 and 15 (16 and 17) inside the at least one fluid reservoir 6 (and 7) when in the upright position or they may be at or below these openings depending on the at least one wick 5 loading requirements. The wick fitting bracket 36 (and 37) may be located in any suitable location on the integrated container 1 so as to accept and provide for a tight seal with the wick fitting 3 (and 4) and the wick 5. The wick fitting 3 (and 4) may be configured to tightly hold the wick 5 as it is placed in the wick fitting bracket 36 (and 37), which may be made to sealably enclose the wick fitting 3 (and 4) and/or the wick 5 to minimize leakage of the volatile material 8 at or from either or both the junctions of the wick fitting 3 (and 4) and the wick 5 or the wick fitting 3 (and 4) and the wick fitting bracket 36 (and 37).

Figure 6:
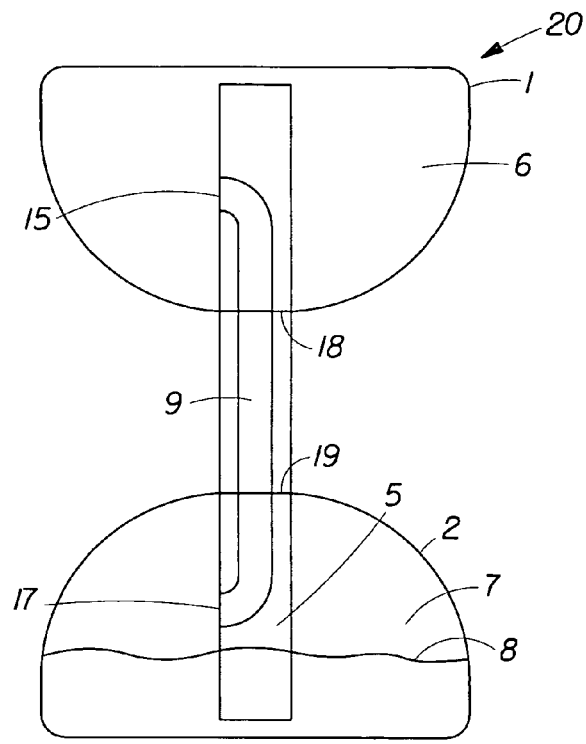

FIG. 6 depicts a cross-section of another non-limiting embodiment of a volatile material delivery system 20 having two containers 1 and 2 which are opposedly-connected and fluidly-connected to each other via the at least one by-pass tube 9, and/or the at least one wick 5. For example, the by-pass tube 9 may be incorporated within the wick 5 itself. It can be located near but not in physical contact with the wick 5 or it can actually be in physical contact the wick 5. One or more by-pass tube opening 15 (and 17) may be located anywhere within the wick 5, the reservoir 6 (and 7), and/or the container 1 (and 2) of the delivery system 20. For example, the by-pass tube 9 can enter the same wick opening 18 (and 19) as the wick 5 but can be made longer and be positioned away from the wick 5 so as to act as an alternative fluid reservoir for collecting volatile material 8 when and if the delivery system 20 is inverted and/or toppled. In another example, the by-pass tube opening 15 (and 17) may be integrated within the wick opening 18 (and 19) such that both the by-pass tube 9 and the wick 5 pass through the same opening. In this case, only one seal (not shown) may be needed to prevent excess volatile material 8 from escaping the delivery system 20 during the boost level emission mode. This will reduce the costs of manufacture and reduce the potential for seal failure or leakage. The by-pass tube 9 also may be made of wick 5 material by simply creating a cavity within the wick 5 itself. There can be more than one by-pass tube 9 and/or wick opening 15 (and 17) in the same reservoir 6 (and 7) and/or in the same wick 5.

Figure 7A:
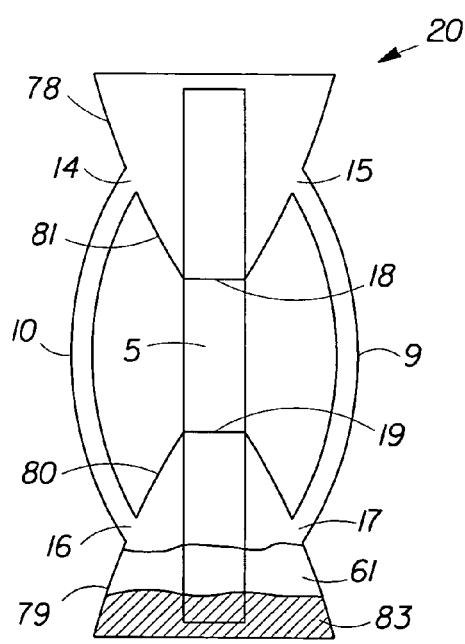

FIG. 7a depicts the cross-section of another non-limiting embodiment of a delivery system 20 in the maintenance level emission mode. The delivery system 20 has two reservoirs 78 and 79, two by-pass tubes 9 and 10, one wick 5, and at least one multi-phase volatile material comprised of two or more separate and distinct phases 61 and 83. Any suitable multi-phase volatile material in any suitable amount, density and/or viscosity may be used. During the maintenance level emission mode, the multi-phase volatile material is stored in the lower fluid reservoir 79. The separate and distinct phases 61 and 83 may be delivered to the atmosphere via capillary action from the fluid reservoir 79 to the at least one wick 5 in any suitable order or sequence. For example, the wick 5 may draw and deliver both phases in equal amounts from the reservoir 79 (and 80) to the atmosphere; and preferentially deliver phase 61 quicker than phase 83, and vice versa. Any other method that causes the wick 5 to preferentially draw and deliver fluid from one of the desired phases at a rate greater than that of the other at rest or equilibrium may be used. For example, the length of the at least one wick 5 may be configured or height positioned within the fluid reservoir 80 such that it preferentially draws phase 61 during the maintenance level emission while at the same time not drawing on phase 83. Other means of providing differential uptake by the wick include, but are not limited to: providing different wick material types and/or designs, and adjusting the chemical properties of the different phases in the multi-phase volatile composition to modify uptake on the wick 5.

Figure 7B:
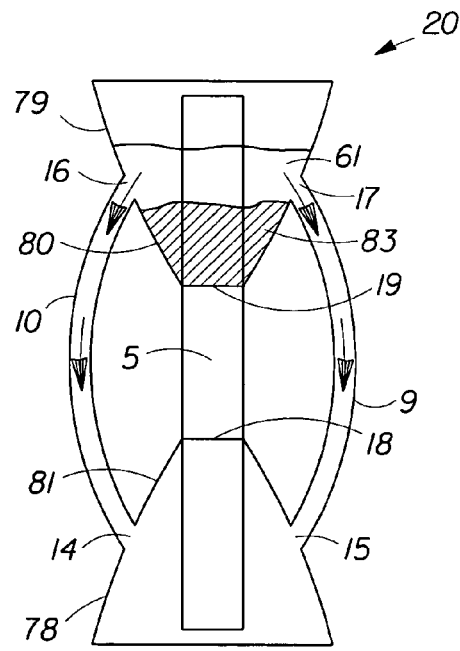

FIG. 7b depicts the delivery system 20 in the boost level emission mode. When a boost level emission is desired, the consumer inverts the delivery system 20. Upon inversion, the lower fluid reservoir 79 (of FIG. 7a) becomes the upper fluid reservoir 79 of FIG. 7b. Whereupon, at least some of the multi-phase volatile material is collected in the unit dose chamber 80 while the excess multi-phase volatile material begins to drain to the lower fluid reservoir 78 via inlet openings 16 and 17 and by-pass tubes 9 and 10. The location of the at least one by-pass tube openings 16 and 17 may allow the consumer to fill the unit dose chamber 80 and/or the at least one wick 5 with a desired fluid phase.

The character, as well as, the intensity of the multi-phase volatile material perceived by the consumer during the boost level emission may change upon mixing and/or displacement of the separate phases 61 and 83 of the multi-phase composition being collected in the unit dose chamber 80. Any suitable physical property or characteristic of the multi-phase volatile material 78 may be used to separate and preferentially load the at least one wick 5 with the desired phase.

The density of the at least two separate and distinct phases of the multi-phase volatile material may control how and when a particular volatile material phase is delivered to the wick 5. For example, though a less dense phase 61 may enter the by-pass tubes 9 and 10 and flow faster upon mixing after inversion than a more dense phase 83, the more dense phase 83 may actually displace some or all of the less dense phase 61 in the unit dose chamber 80 given the proper configuration and/or conditions. When a portion of the more dense phase 83 displaces a portion of the less dense phase 61 in the unit dose chamber 80, the displaced less dense phase 61 may then be drained back to the lower fluid reservoir 78. During the boost level emission mode, the more dense phase 83 is preferentially delivered to the wick 5 and emitted to the atmosphere over the less dense phase 61. Thus, the same multi-phase volatile material at the maintenance level emission mode may exhibit a different character and/or intensity during the boost level emission mode.

Similarly, the viscosity of the at least two separate and distinct phases of the multi-phase volatile material (not shown) may control how and when a particular volatile material phase is delivered to the wick. For example, at equilibrium during the maintenance level emission, the wick may be located at a specific height or in a specific position in the lower fluid reservoir so as to draw from the more viscous phase of the two or more volatile materials. Upon mixing during the boost level emission, the lower fluid reservoir becomes the upper fluid reservoir. Since the less viscous phase may flow faster than the more viscous volatile material, the unit dose chamber may be first filled with the less viscous phase. The more viscous volatile material, being slightly less or of similar density with the less viscous phase, is directed to the by-pass tubes and collected by the lower fluid reservoir via gravity. Thus, during the boost level emission mode, the less viscous volatile material is preferentially delivered to the wick and emitted to the atmosphere over the more viscous phase.

Figure 8A:
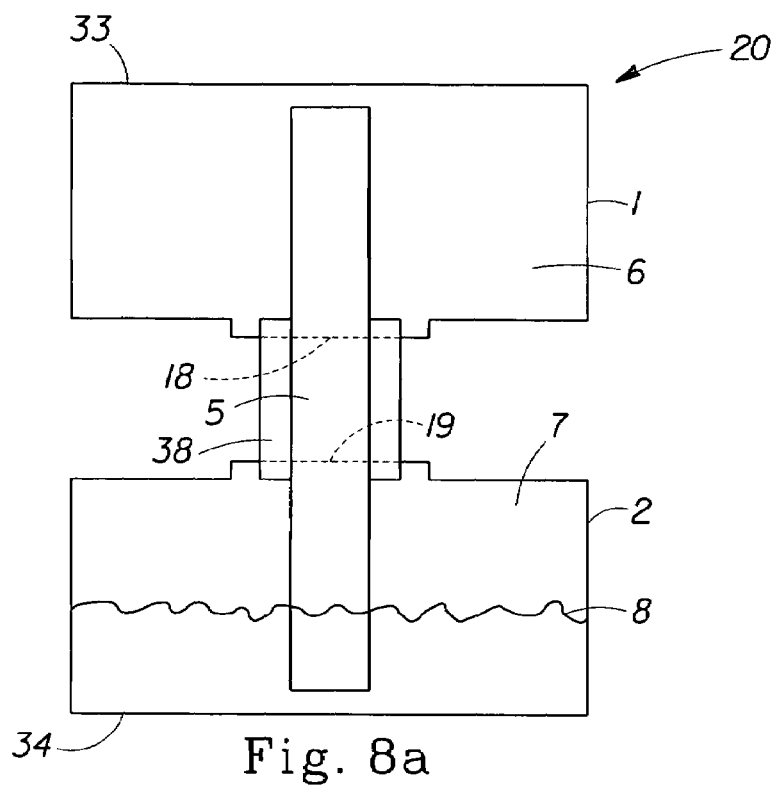

FIG. 8a depicts the cross-section of another non-limiting embodiment of the volatile material delivery system 20 having at least one secondary wick 38. The at least one secondary wick 38 may be loaded with volatile material 8 at any time, for example, upon inversion of the delivery system 20 or by non-aerosol pump to deliver a boost level emission. The secondary wick 38 may aid in the delivery of an increased intensity of volatile material 8 to the atmosphere by increasing the evaporative surface area during the boost level emission mode. The secondary wick 38 made of any suitable material in any suitable size, shape, or configuration. For example, the secondary wick 38 may in the shape of a flat washer, hollow ring, or doughnut, extending at least partially within the at least one fluid reservoir 6 (and 7) such as, just beyond the junction of the at least one wick opening 18 and 19 as shown. The secondary wick 38 may also be extended to any position within the fluid reservoir 6 (and 7), such as, to the full length of the interior fluid reservoir 6 (and 7) cavity, perhaps even touching the interior surface of the container base 33 (and 34). In this example, the secondary wick 38 may be in physical contact with the primary wick 5.

Figure 8B:
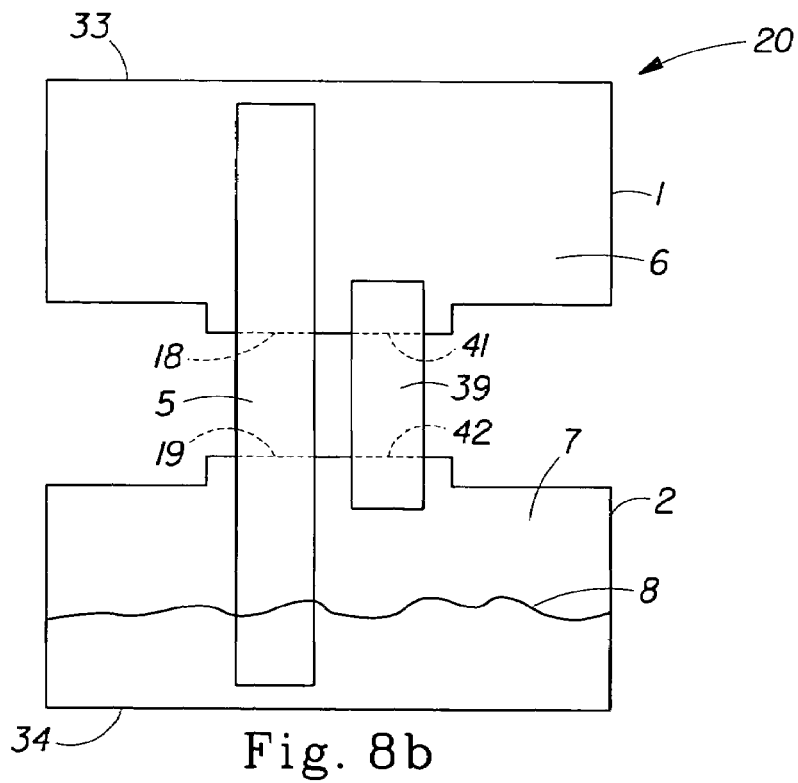

FIG. 8b depicts the cross-section of another non-limiting embodiment of the volatile material delivery system 20 having at least one secondary wick 39 not in physical contact with the primary wick 5.

Figure 8C:
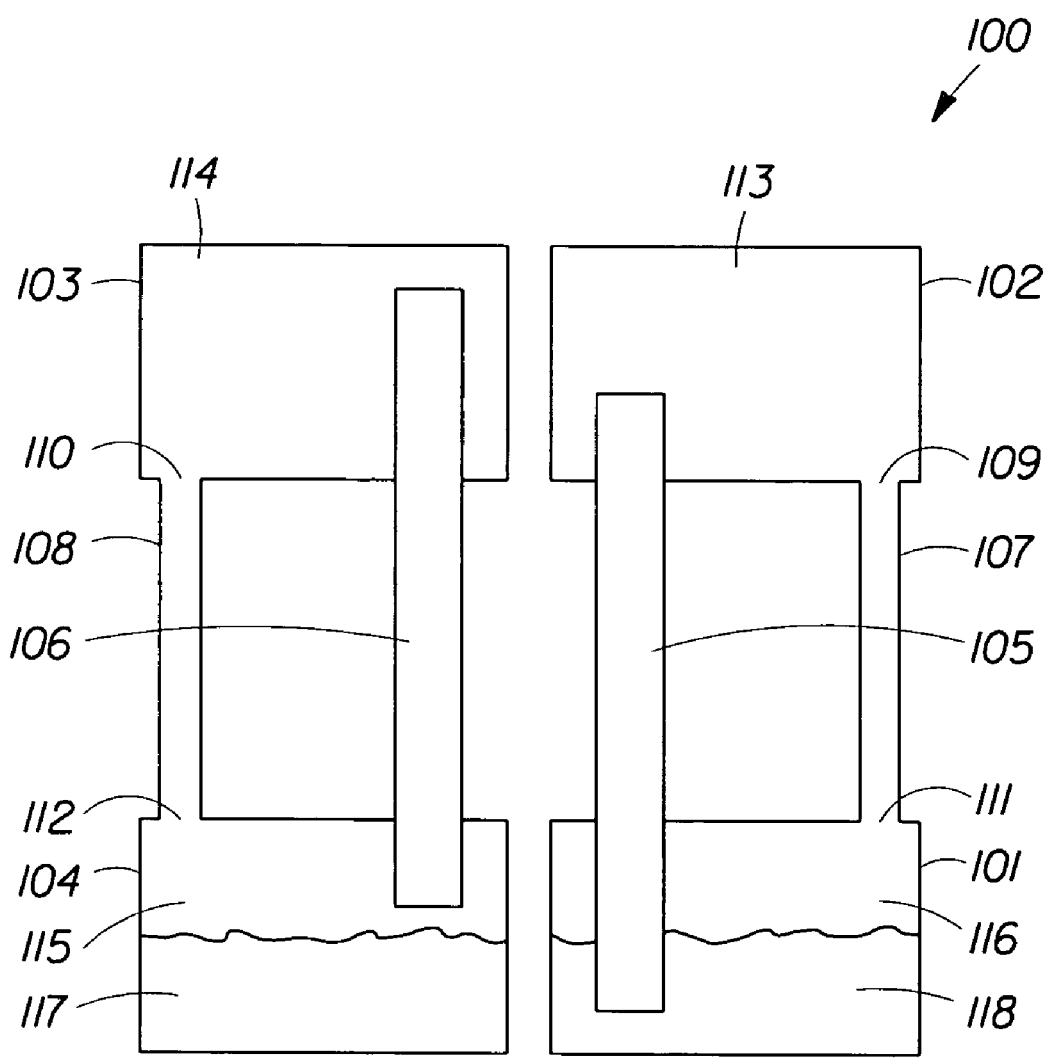

FIG. 8c depicts the cross-section of another non-limiting embodiment of a multiple delivery system 100 having a plurality of individual delivery systems. For example, the delivery system 100 may comprise of a plurality of separate containers 101, 102, 103 and 104 in any configuration, not all of which are physically-connected, opposedly-connected, or fluidly-connected. Containers 101 and 102 may be opposedly-connected, and/or fluidly-connected, but not necessarily physically-connected to containers 103 and 104, yet all may be housed in a single delivery system 100 or housing (not shown). Each pair of containers 101 and 102, and 103 and 104 may contain at least one reservoir or a pair of reservoirs 113 and 116, and 114 and 115, and respectively. Each pair of reservoirs 113 and 116, and 114 and 115 may have at least one by-pass tube 107 (and 108) and corresponding by-pass tube openings 109 and 111, (110 and 112) that fluidly-connects the opposing reservoir pairs as described above. In this embodiment, different volatile materials may be provided in each of the fluid reservoir pairs. For example, volatile material 117 may be provided in reservoir pair 113 and 116, while volatile material 118 may be provided in reservoir pair 114 and 115.

The position, location, size, shape, and configuration of the individual wick 105 (and 106) may vary according to the requirements of each individual delivery system housed in the multiple delivery system 100. For example, wick 105 may be positioned in reservoir 116 so that the wick 105 extends the full length of the interior fluid reservoir 116 cavity of container 101 while the wick 105 extends only partially within the interior fluid reservoir 113 cavity of container 102. Similarly, wick 106 may be positioned in reservoir 114 so that the wick 106 extends the full length of the interior fluid reservoir 114 cavity of container 103 while the wick 106 extends only partially within the interior fluid reservoir 115 cavity of container 104.

In this configuration, a different fragrance may be emitted from each individual delivery system during the two separate maintenance level emission modes. In the first maintenance level emission mode (A), wick 105 is immersed in volatile material 118 while at the same time wick 106 is non-immersed in volatile material 117. Thus, only wick 105 is active, emitting volatile material 118 via capillary action. When the boost level emission mode is desired, the multiple delivery system 100 is inverted. The lower fluid reservoirs 115 and 116 become the upper fluid reservoirs. In the boost level emission mode, wicks 105 and 106 are individually loaded and/or dosed with the volatile material 118 and 117, respectively. When the boost level emission mode is completed and the volatile material 117 (and 118) drains to their respective lower reservoir pairs 114 (and 113) via either the by-pass tube 107 (and 108) or wick 105 (and 106), the second maintenance level emission mode automatically begins.

In the second maintenance level emission mode (B), wick 106 is immersed in volatile material 117 while at the same time wick 105 is non-immersed in volatile material 118. Thus, only wick 106 is active, emitting volatile material 117 via capillary action. Thus, the character of the boost level emission is different than both maintenance level emissions (A) and (B) which may be in turn be different in character from themselves.

Figure 9D:
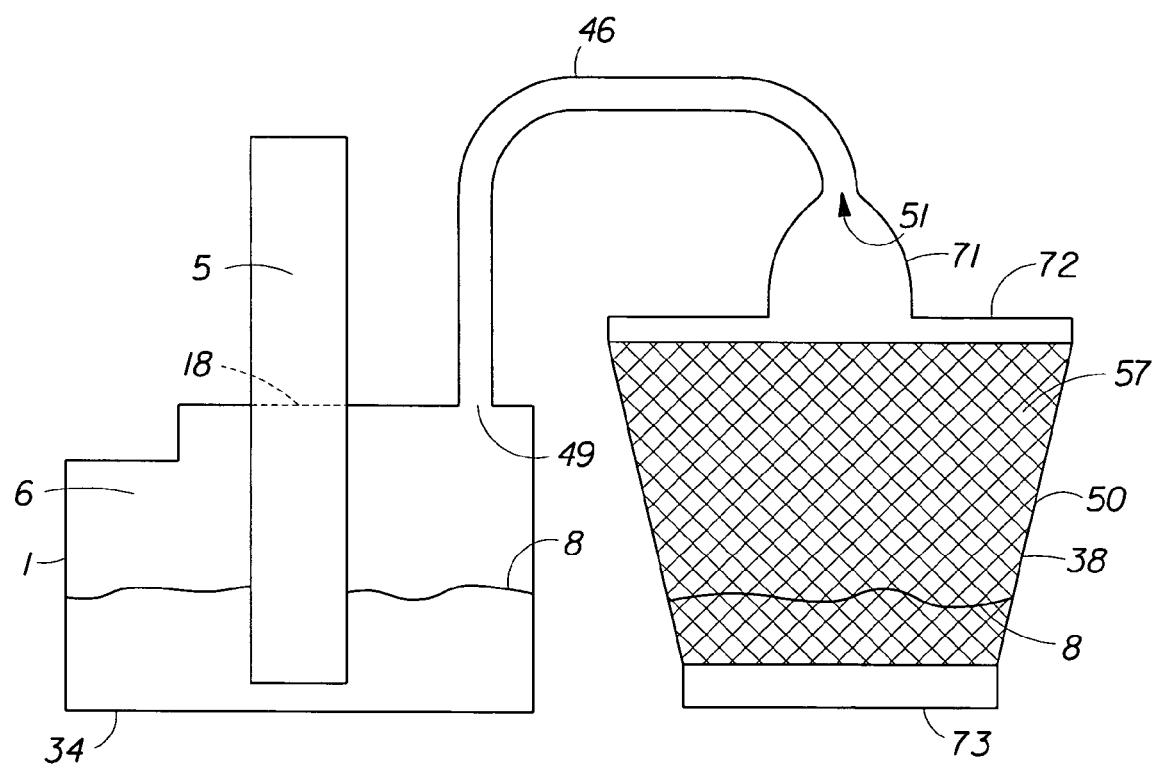

FIGS. 9a, 9b, 9c, and 9d depict the cross-sections other non-limiting embodiments having a single container 1, at least one fluid reservoir 6 and at least one dosing tube 45 in the maintenance level emission mode. When the boost level emission mode is desired, the inversion of the delivery system 20 in FIG. 9a is required to load and/or doses the wick 5 with a volatile material 8. The wick 5 is at least partially located inside the at least one fluid reservoir 6 and is fluidly-connected to at least some of the volatile material 8 that is stored in the at least one fluid reservoir 6. Upon inversion, the dosing tube inlet opening 49 collects the volatile material 8, located within the fluid reservoir 6, in the dosing tube 45, which becomes at least partially filled with the volatile material 8. When the delivery system 20 is returned to the upright position by being placed back on its container base 34, at least some portion of the volatile material 8 is collected by the dosing tube 45. The collected portion of volatile material 8 then flows by gravity to the wick 5 via the dosing tube outlet opening 51 which is physically and/or fluidly-connected to the wick dosing chamber 54 which in turn is physically and/or fluidly-connected to the wick 5 and/or the at least one secondary wick 38. The wick dosing chamber 54 allows the volatile material 8 to wet the wick 5 and the secondary wick 38 with at least some of the volatile material 8 collected in the dosing tube 45 after inversion for delivery of the boost level emission. It should be noted that delivery of the maintenance level emission in this embodiment requires no mechanical action, such as inversion. The capillary loading of the wick 5 automatically returns after inversion. The capillary action automatically may continue until the delivery system 20 is substantially exhausted of the volatile material 8 by the emission processes.

Like the embodiment of FIG. 9*a*, the embodiment of FIGS. 9*b* and 9*c* also require no mechanical step to deliver the maintenance level emission. However, unlike the previous embodiment, the boost level emission is accomplished by loading the wick 5 and/or secondary wick 38 (and 39) with volatile material 8 via a squeezable bladder 47 or non-aerosol pump 48. FIG. 9*b* uses the squeezable bladder 47, which draws at least some volatile material 8 from the fluid reservoir 6 of container 1 via the dosing tube inlet opening 49. The volatile material 8 is collected in the dosing tube 45 and is collected in the bladder 47 via the bladder inlet opening 52 and is discharged to the dosing tube 46 via the bladder outlet opening 53 when the bladder is squeezed. The wick 5 and the optional secondary wick material (not shown) may be loaded or dosed according to the method described above in FIG. 9*a*.

Like the embodiment of FIG. 9*b*, the embodiment of FIG. 9*c* uses the same delivery concept except the squeezable bladder 47 is replaced with a non-aerosol hand pump 48. The non-aerosol hand pump 48, having pump inlet opening 56 and pump outlet opening 55, may be of any suitable type, size, shape, and/or dimension having a suitable pump head such that at least some volatile material 8 is delivered to the wick 5 and/or the secondary wick 38 and 39 when the non-aerosol hand pump is used with minimal mechanical effort. There is no sprayer attached to any pump or squeezable bladder device.

FIG. 9*d* depicts the cross-section another non-limiting embodiment of a delivery system 20 having two separate containers 1 and 50. The wick 5 is fluidly-connected to the volatile material 8 stored in the fluid reservoir 6 via the sealable wick opening 18. A maintenance level emission is provided by capillary action of the volatile material 8 via the at least one wick 5 to the atmosphere. The wick 5 may be of any suitable size or length and may extend within the reservoir 6 to the interior surface of the container base 34. Container 50 is fluidly connected to container 1 via a dosing tube 46. Container 50 may comprise a dosing funnel 71, a dosing diffuser 72, a collection base 73, a secondary fluid reservoir 57, and a secondary wick 38. When a boost level emission is desired, the volatile material 8 of container 1 may be delivered to the secondary wick 38 of container 50 by any suitable means. The volatile material 8 is delivered to the dosing tube 46 via the dosing tube inlet opening 49. The volatile material 8 enters container 50 via the dosing tube outlet opening 51 where it is collected by an dosing funnel 71, which directs the volatile material 8 to the dosing diffuser 72, which delivers the volatile material 8 to the secondary wick 38. The secondary wick 38 is fluidly connected to the dosing diffuser 72 and the dosing funnel 71. The secondary wick 38 may also be fixedly connected to the dosing diffuser 72 and the container base 73 via any suitable connection.

The secondary wick 38 may be any suitable size or shape. For example, the secondary wick may be in the shape of a hollow cup, sphere or ring wherein the volatile material 8 flows by gravity from the dosing diffuser 72 through the secondary wick 38 to the container base 73. The secondary wick 38 may comprise from any suitable surface area. For example, a suitable surface area may range from about 1 to about 100 times, or from about 1 to about 50 times, or from about 1 to about 20 times, or from about 1 to about 5 times more surface area than the at least one wick 5. The increase in wick surface area may be provided by any suitable means, such as by varying the pore size of the wick material or by pleating or folding the wick material.

Like the embodiments in FIG. 9*a*, the embodiment of FIG. 9*d* may initiate the boost level emission by inversion (or by any other suitable means) of container 1 such that volatile material 8 is delivered to the secondary wick 38 for boost level emission. Excess volatile material 8 that is not collected onto the secondary wick 38 after being delivered via the dosing diffuser 72 may be collected in the secondary fluid reservoir 57, which is fluidly connected to the secondary wick 38. The secondary wick 38 may also be a porous solid, having an optional secondary fluid reservoir 57. The porous solid may absorb excess volatile material 8 not immediately emitted from the secondary wick 38 itself. The boost level emission will last until all of the volatile material 8 evaporates. For example, all the volatile material 8 that is loaded onto the secondary wick 38 or that is stored in the secondary fluid reservoir 57 will be delivered to the atmosphere via evaporation during the boost level emission.

Figure 10A:
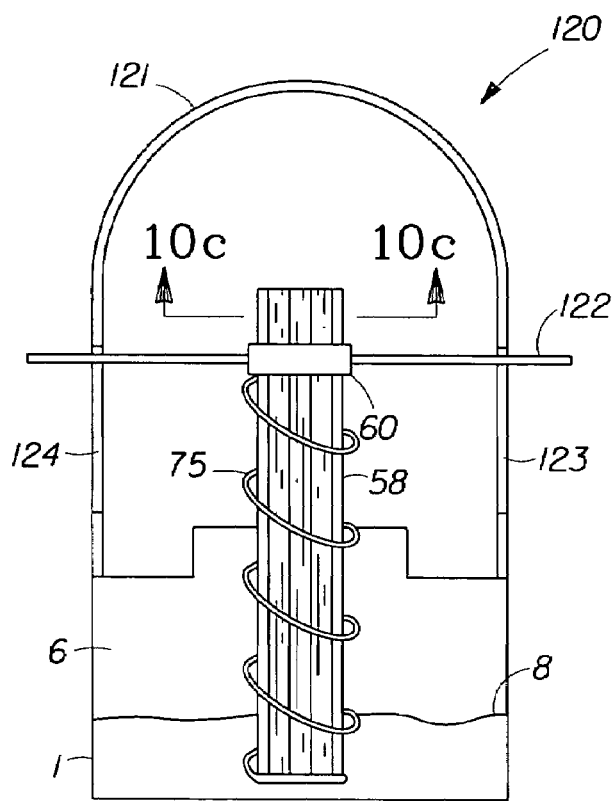
Figure 10B:
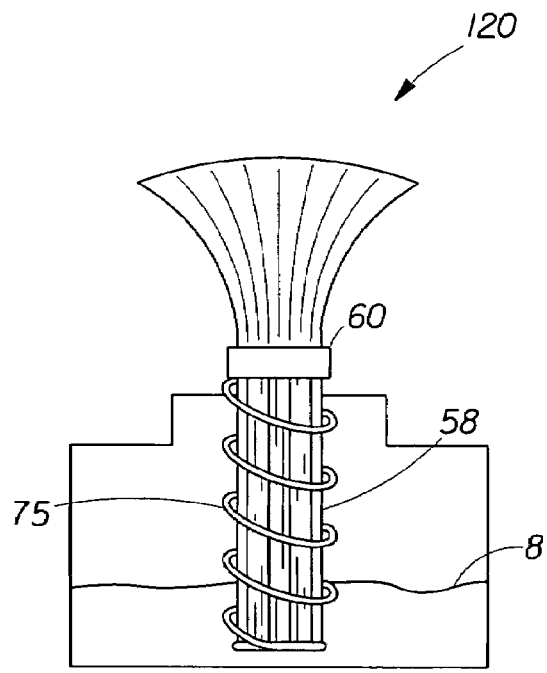
Figure 10C:
FIG. 10c shows a cross-section of a pleated wick.

FIGS. 10*a* and 10*b* depict the cross-sections another non-limiting embodiment of a delivery system 120 having an adjustable, high-surface area wick 58 that can deliver more or less volatile material 8 to the atmosphere depending on the amount of surface area exposed to the atmosphere. FIG. 10*a* represents the delivery system 120 at the equilibrium state wherein the least amount of surface area of the wick 58 is exposed to the atmosphere. The spring 75 is uncompressed in its equilibrium state. In the folded position at equilibrium, the wick 58 provides the maintenance level emission.

In certain embodiments, the delivery system 120 comprises a wick spring assembly comprising an adjustable, high-surface area wick 58, a wick retraining ring 60, a spring 75, an optional damping device (not shown), a spring restraining device (not shown), optionally, a perforated protective shell 121, and at least one lever 122 for compressing the spring 75 via the wick restraining ring 60. The perforated protective shell 121 may be made of any suitable material in any size, shape, or configuration so as to allow for unrestricted emission flow of volatile material via the perforations (not shown), which may be any suitable size, shape or configuration. For example, the perforations (not shown) may be a plurality of slots. The perforated protective shell 121 may provide for a vertical slot 123 that allows the lever 122, which is attached to the wick restraining ring 60, to travel the full length required for spring 75 compression. The wick spring assembly allows the consumer to configure or adjust the exposed surface areas of wick 58 in order to vary the intensity of the boost level emission. While using the lever 122 to compress the spring 75, the consumer may deliver the boost level emission without having to invert the delivery system 120.

FIG. 10*b* represents the delivery system 120 in the maximum boost level mode. Here the greatest amount of surface area of the wick 58 is exposed to the atmosphere. The spring 75 is fully compressed. The wick 58 may be made of any suitable material in any suitable shape or size such that when it is unrestrained, it opens or unfolds to expose its greatest surface areas to the atmosphere. As the spring 75 gradually returns to its equilibrium length, the surface area of the wick is reduced by the wick restraining ring 60. The optional spring damping device (not shown) will allow variable boost level emission durations to be provided. When the wick spring to its equilibrium state, the boost level emission mode ceases and the maintenance level emission mode automatically returns. Thus, the duration and intensity of the boost level emission may be controlled by the consumer by simply depressing the lever 122 to the desired position.

Figure 11:
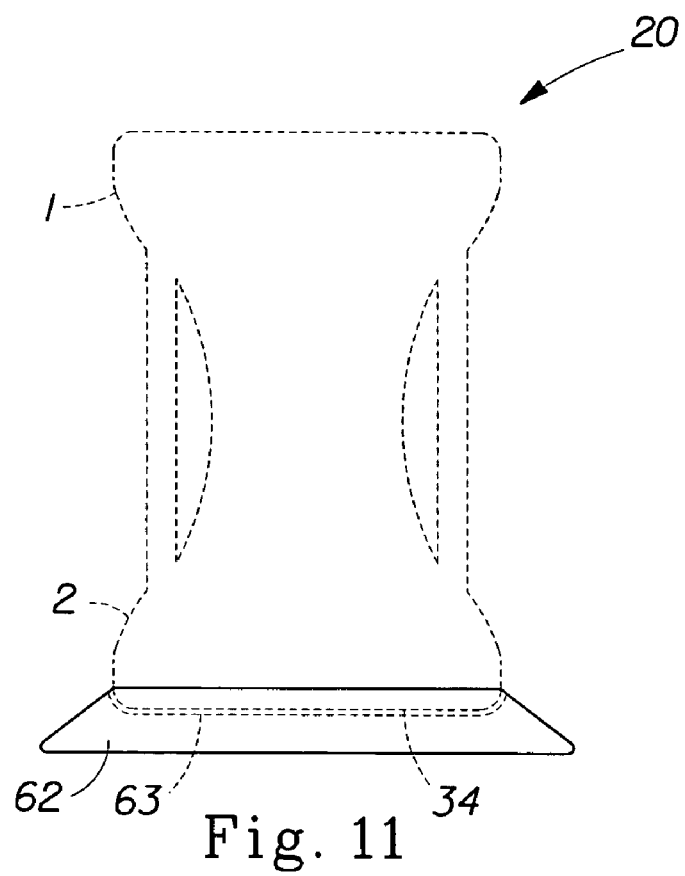

FIG. 11 depicts the cross-section of another non-limiting embodiment of a delivery system 20 having a stability cradle 62. The stability cradle 62 may be made of any suitable material having any suitable size, shape, or configuration, such that the delivery system 20 is at least partially stabilized in a suitable dispensing position (for example, an upright positions) once placed in the stability cradle 62. The upright position in this case refers to any inclination greater than 45 degrees from vertical in any direction. For example, the stability cradle 62 made be made of wood, metal, plastic and/or glass and may optionally have a recessed area 63 which when in contact with the at least one container base 34 adds at least some stability to the delivery system 20. The stability cradle 62 allows consumers the convenience of identifying a setting for the delivery system 20 in any room or location needing treatment (for example, living room, kitchen, bathroom, garage, backyard, etc.). The stability cradle 62 may allow for decorative items to be placed onto the structure in order to allow the consumer to personalize the delivery system 20. For example, a colored veneer may be selected having many different decorative colors available for color coordination. The decorative items may be attached anywhere on the stability cradle 62 and/or delivery system 20 by any fastening means, such as fasteners, adhesives, lock and key devices, etc.

Figure 12:
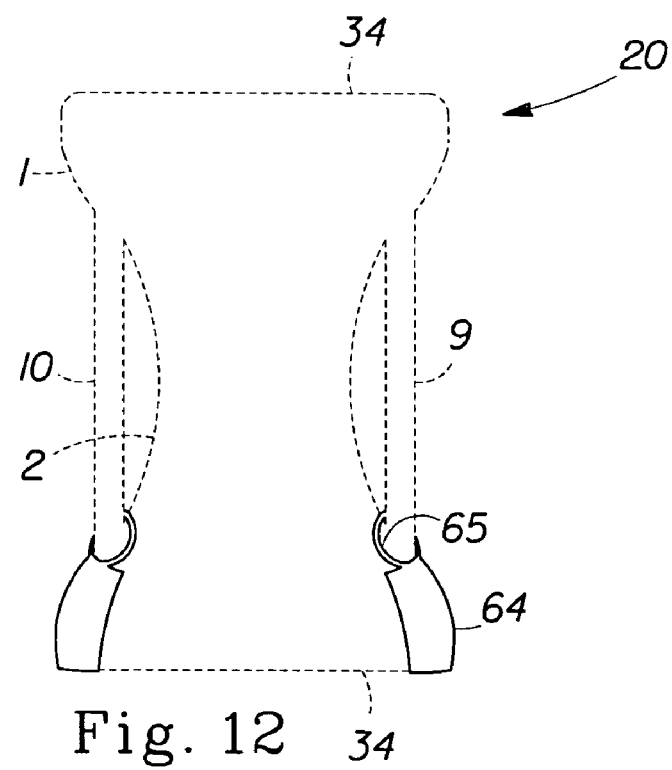

FIG. 12 depicts the cross-section of another non-limiting embodiment of a delivery system 20 having at least one ballast 63 which may be made of any suitable material in any size, shape, or configuration, so as to provide at least some stability against overturning once the delivery system 20 is overturned by touching, shaking, unleveling toppling, or otherwise. Suitable forms of suitable ballast materials include, but are not limited to: solids, liquids, gels, powders, granules, and combinations thereof. For example, the ballast 63 may comprise any suitable material having any suitable weight in order to reduce overturning of the delivery system 20. The ballast 63 may be attached to the delivery system 20 and/or the container 1 (and 2) in any suitable manner (for example, fixed, non-fixed, etc). The ballast 63 may be removably attached to allow adjustment on the delivery system 20. Thus, the ballast 63 may be positioned and/or repositioned on the container 1 (and 2) in any suitable configuration and by any suitable means. For example, the consumer may attach the ballast 63 to the lower container 2 after inversion. Alternatively, the manufacturer may attach the ballast 63 so that it may automatically be repositioned from the upper container 1 to the lower container 2 by the action of gravity when the at delivery system 20 is inverted.

The ballast 63 may be connected to the at least one container via any suitable mechanism, for example a sliding mechanism. The ballast 64 may freely move along a longitudinal axis of the delivery system 20 by gravity, for example, by sliding along the by-pass tube 9 (and 10) via an attachment device 65, such as a ring. Alternatively, the ballast 64 may be physically relocated, without sliding, for example, by clipping the ballast 64 to any portion of the delivery system 20, such as to the lower container base 34 or to the by-pass tube 9 (and 10), before, during, or after the inversion process. A suitable attachment device 65 can be made of any suitable material in any suitable size, shape, or configuration. For example, the attachment device 65 may be a clamp, clip, ring, string, tie, adhesive material, friction fitting, magnet, and combinations thereof. The at least one ballast 63 may also be attached and/or connected to the at least one container 1 (and 2) in a fixed position. In one non-limiting embodiment, the ballast (not shown) may be in the form of sand or a ball bearing that is housed in a component of the delivery system 20.

Figure 13A:
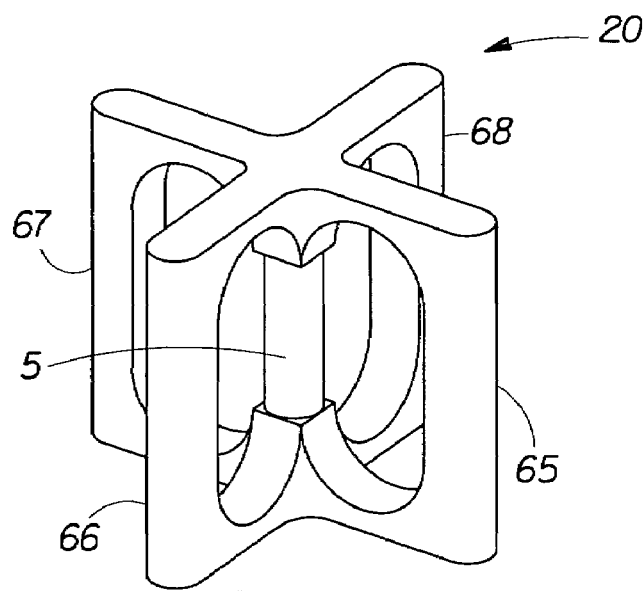
FIGS. 13a and 14 show perspective views of a delivery system.
Figure 13B:
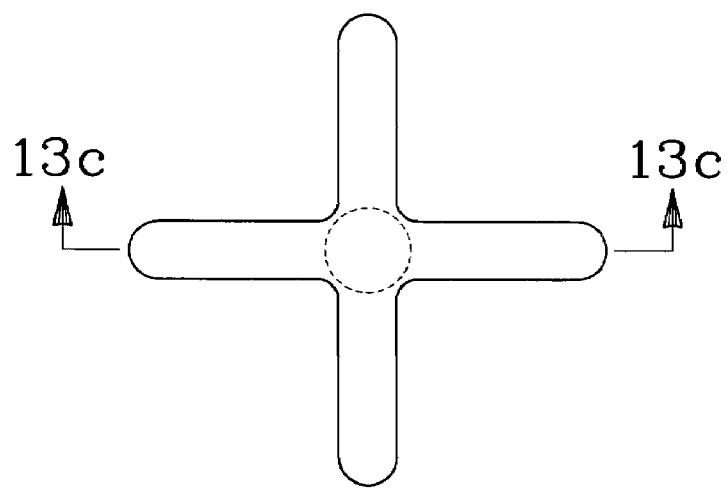
FIG. 13b shows a top view of a delivery system.
Figure 13C:
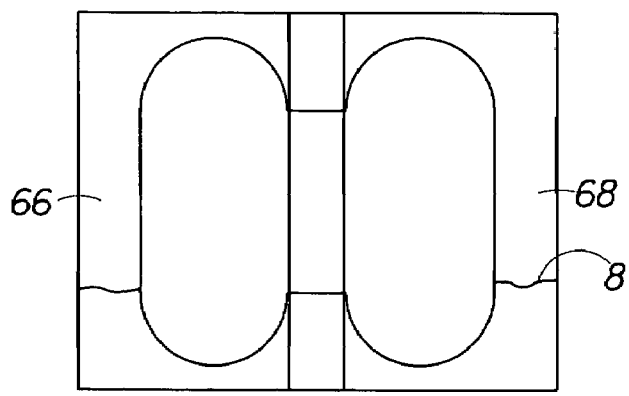

FIG. 13a depicts a perspective view of another non-limiting embodiment of a delivery system 20 having four by-pass tubes 65, 66, 67, and 68 and at least one wick 5. When overturned over, the by-pass tubes 65, 66, 67, and 68 may act as secondary fluid reservoirs to collect some of the volatile material (not shown) that was stored in either fluid reservoir (not shown) and thereby minimize leakage from the delivery system 20. FIG. 13b shows the top view of the delivery system 20 of FIG. 13a. This configuration aids in stabilizing the delivery system 20 after toppling from the upright position. FIG. 13c shows the cross-section view (A-A) through the by-pass tubes 66 and 68.

Figure 14:
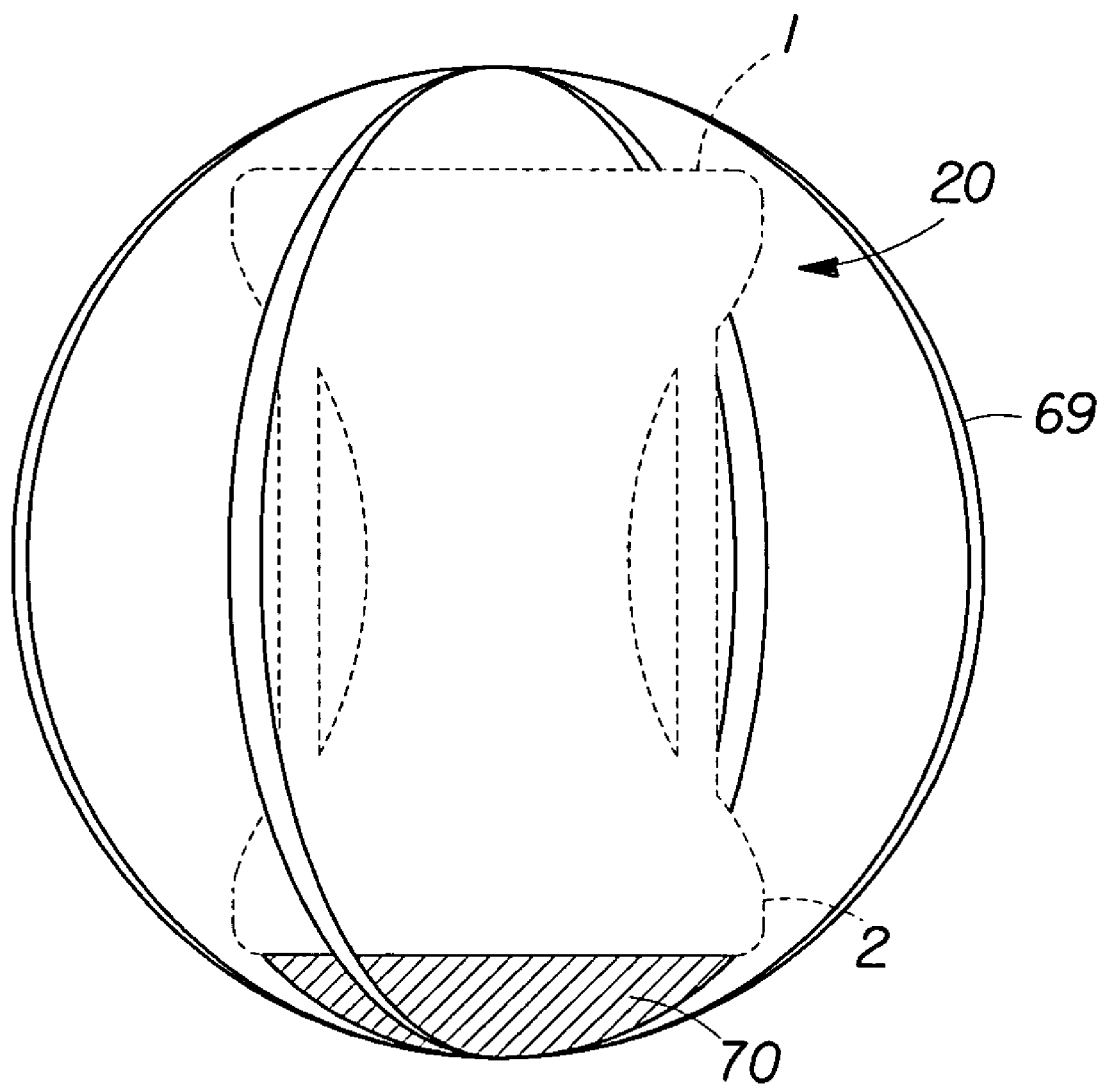

FIG. 14 depicts a perspective view of another non-limiting embodiment of a delivery system 20 having an external frame 69 having at least one ballast 70. The external frame 69 may be made of any suitable material and configured in any suitable size or shape. The external frame 69 may be removeably attached to the delivery system 20 by any suitable means. The ballast 70 may also be removably attached to the external frame 69. The delivery system 20 may be easily removed from the external frame 69 and inverted by the consumer before reattaching. Alternatively, the delivery system 20 may be inverted in place. For example, the external frame 69 may provide a means to invert the delivery system 20 by providing a pivoting arm (not shown) which allows the consumer to simply invert the delivery system 20 by pushing on the container 1 (and 2). The ballast 70 may be removed after the delivery system 20 and reattached to the external frame 69 as needed, for example, for cleaning.

Figure 15A:
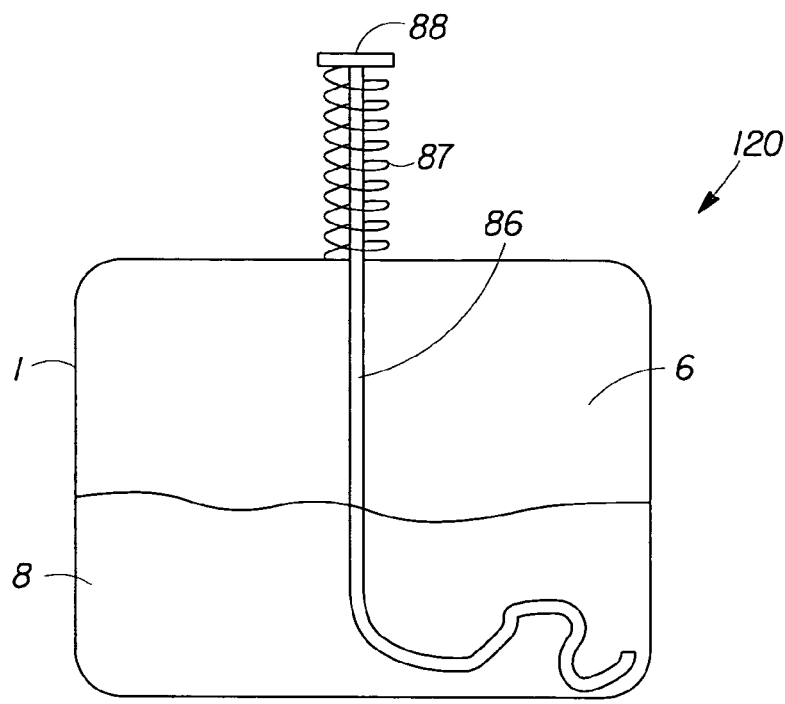

FIG. 15a depicts a cross-section of a delivery system 20 comprising another wick spring assembly mechanism. The wick spring assembly comprises at least one retractable wick 86, at least one spring 87, at least one spring adjuster 88, an optional damping device (not shown), and a spring restraining device (not shown). Like the embodiment of FIG. 10a, the maintenance level emission mode occurs at the equilibrium state where the least amount of surface area of the retractable wick 86 is exposed to the atmosphere. At equilibrium, the retractable wick 86 is immersed in the volatile material 8 contained in the fluid reservoir 6 of the container 1. In this case, the wick spring assembly 75 would be compressed in the equilibrium state.

When a boost level emission is desired, more surface area of the retractable wick 86 is exposed to the atmosphere. For example, the consumer may increase the wick surface area by pulling up on the spring adjuster 88 to the desired length and thereby exposing more retractable wick 86 surface area to the atmosphere than is exposed at equilibrium. When the retractable wick 86 is fully extended, the wick spring 75 is uncompressed. The volatile material 8 emission rate increases as a function of the amount of wick surface area exposed. The more surface area exposed, the higher the boost level emission rate. Thus, the consumer has the ability to control perceived intensity levels during the boost level emission mode by varying the amount of retractable wick 86 surface area exposed. As the wick spring assembly 75 gradually compresses back to the equilibrium state, the retractable wick 86 is returned to the fluid reservoir 6 of container 1 where it is again immersed in and reloaded with the volatile material 8. Thus, the boost level emission may be uniformly delivered, being repeated as many times as necessary by the consumer until the volatile material 8 is exhausted.

Figure 15B:
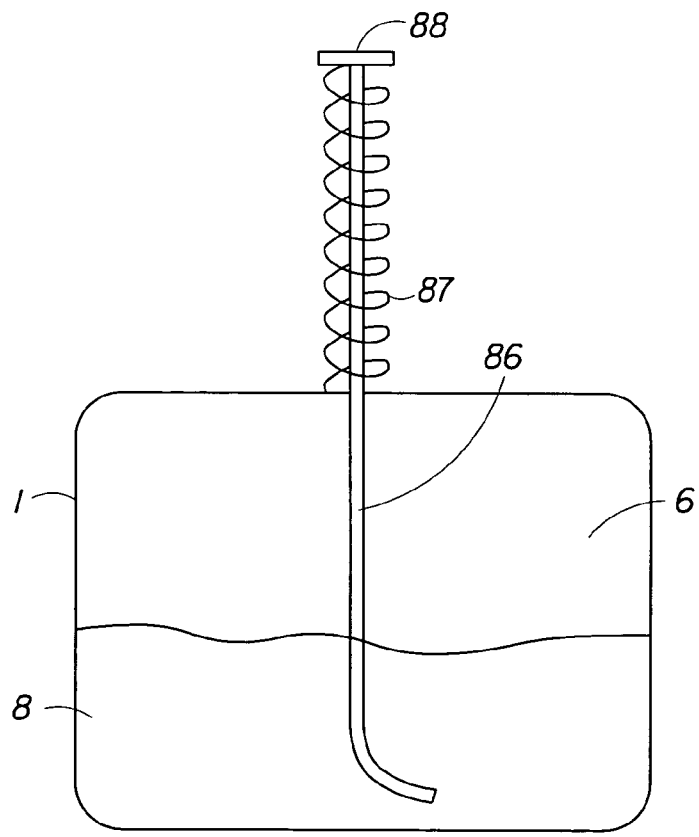

Any other suitable means of increasing the intensity of the boost level emission is also useful. For example, in certain other embodiments, the volatile material in the delivery system may be in the form of a gel or liquid gel (not shown). In such a case, the wick may be modified to facilitate the loading of the volatile gel composition onto the wick, the spring itself, and/or onto a suitable delivery device such as, paddles, which can be attached onto or adjacent to the wick spring. The gel-laden wick spring itself and/or the delivery device can provide the means to deliver boost level emission. At equilibrium, evaporation of the volatile gel composition from off the top layer surface of the wick and/or volatile gel material would provide the maintenance level emission mode. Conversely, as the gel-laden wick spring is extended away from the container in the uncompressed mode (similar to the embodiment of FIG. 15b), more surface area evaporation of the volatile gel material would occur. As the wick spring gradually returns to equilibrium, the boost level emission would automatically cease while the maintenance level emission would automatically return.

In other alternative embodiments, the delivery system can comprise a kit containing a bundle or packs of one or more volatile materials. Any of the foregoing embodiments may be used in supplying consumers with their initial product(s), as well as with refills for the same. In certain non-limiting embodiments, the delivery system may comprise supplying consumers with a choice of different types of volatile materials (for example, a fragrance composition, a malodor reducing composition, an insecticide, a mood enhancer composition, or combinations thereof) other than, or in addition to, the volatile materials sold in the initial product(s).

The disclosure of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

It should be understood that every maximum numerical limitation given throughout this specification would include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

While particular embodiments of the subject invention have been described, it will be obvious to those skilled in the art that various changes and modifications of the subject invention can be made without departing from the spirit and scope of the invention. In addition, while the present invention has been described in connection with certain specific embodiments thereof, it is to be understood that this is by way of illustration and not by way of limitation and the scope of the invention is defined by the appended claims which should be construed as broadly as the prior art will permit.

What is claimed is:

1. A method of releasing at least one volatile material to the atmosphere, the steps of said method comprise (a) providing a non-energized volatile material delivery system, and (b) delivering a continuous maintenance level emission of at least one volatile material, and a temporary boost level emission of at least one volatile material, wherein said boost level emission is delivered by one or more of the following means: inversion, pumping, or spring-action; wherein said delivery system comprises:
   a) at least one container comprising at least one fluid reservoir;
   b) at least one evaporative surface device opening located in said at least one container having at least some longitudinal exposure;
   c) at least one evaporative surface device which is at least partially located in said at least one evaporative surface device opening and in said at least one fluid reservoir; wherein said at least one evaporative surface device is fluidly connected to said volatile material;
   d) a by-pass tube comprising at least one by-pass tube opening connected to said at least one fluid reservoir for collection of excess volatile material not delivered to said at least one evaporative surface device, wherein said by-pass tube and said at least one evaporative surface device terminate within said at least one evaporative surface device opening, wherein said by-pass tube is in fluid communication with at least some of said excess volatile material not contained in one or more of the following: said fluid reservoir, said unit dose chamber or said at least one evaporative surface device, wherein said delivery system is free of a source of heat, gas, or electrical current, and wherein said at least one volatile material is not mechanically delivered by an aerosol.

* * * * *